United States Patent [19]

Hayashi et al.

[11] 4,128,720

[45] Dec. 5, 1978

[54] PROSTAGLANDIN ANALOGUES

[75] Inventors: Masaki Hayashi; Seiji Kori, both of Takatsuki; Hajimu Miyake, Suita, all of Japan

[73] Assignee: Ono Pharmaceutical Company, Osaka, Japan

[21] Appl. No.: 657,125

[22] Filed: Feb. 11, 1976

[30] Foreign Application Priority Data

Feb. 14, 1975 [GB] United Kingdom ............... 6385/75

[51] Int. Cl.$^2$ ............................................. C07C 177/00
[52] U.S. Cl. .................................. 560/9; 260/327 M; 260/327 C; 562/426; 562/500; 562/503; 260/343.3 P; 260/345.8 P; 536/103; 260/345.7 P; 260/347.2; 260/347.3; 260/347.4; 560/118; 560/121
[58] Field of Search ............................ 260/516; 560/9

[56] References Cited

FOREIGN PATENT DOCUMENTS 7313322   3/1974   Netherlands ............................. 260/473

Primary Examiner—Paul J. Killos
Attorney, Agent, or Firm—Albert H. Graddis; Frank S. Chow

[57] ABSTRACT

Prostaglandins of the formula:

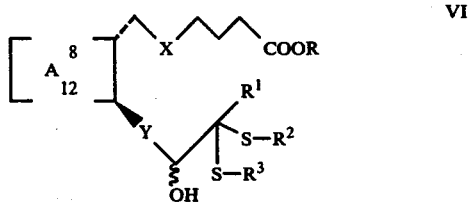

VI wherein A represents a grouping of the formula:

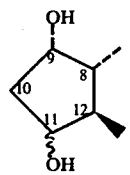

or

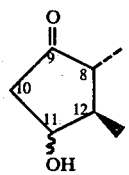

VIIA        VIIB

X represents ethylene or cis-vinylene, Y represents ethylene or trans-vinylene, R represents a hydrogen atom or a straight- or branched-chain alkyl group containing from 1 to 12 carbon atoms, $R^1$ represents a hydrogen atom or a straight- or branched-chain alkyl group containing from 1 to 10 carbon atoms, $R^2$ represents a straight- or branched-chain alkyl group containing from 1 to 4 carbon atoms, $R^3$ represents a straight- or branched-chain alkyl group containing from 1 to 4 carbon atoms, a cycloalkyl group containing from 4 to 7 carbon atoms, or a grouping of the formula:

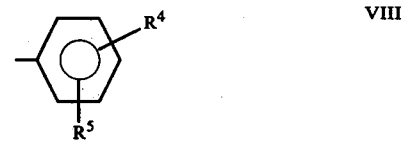

VIII wherein $R^4$ and $R^5$ each represents a hydrogen or halogen atom, a trifluoromethyl group or an alkyl group containing from 1 to 3 carbon atoms, or $R^2$ and $R^3$ together represent an ethylene or trimethylene group and cyclodextrin clathrates of such acids and esters and, when R represents a hydrogen atom, non-toxic salts of such acids, are disclosed.

These compounds exhibit characteristic prostaglandin activity, in particular, inhibitory activity on gastric secretion, luteolytic activity and so on.

5 Claims, No Drawings

PROSTAGLANDIN ANALOGUES

This invention is concerned with new prostaglandin analogues.

Prostaglandins are derivatives of prostanoic acid which has the following formula:

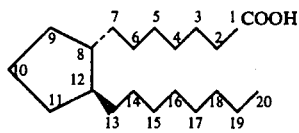
I

Various types of prostaglandins are known, the types depending inter alia on the structure and substituents on the alicyclic ring. For example, the alicyclic rings of prostaglandins F(PGF) and E(PGE) have the structures:

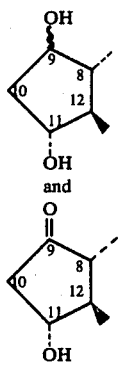

II and

III respectively. In the foregoing formulae and in other formulae throughout this specification the dotted lines denote, in accordance with generally accepted rules of nomenclature, that the attached grouping lies behind the general plane of the ring system, i.e. that the grouping is in α-configuration, the thickened lines ⧹ denote that the grouping lies in front of the general plane of the system, i.e. that the grouping is in β-configuration, and the wavy line ∿ indicates that the grouping is in α- or β-configuration.

Such compounds are sub-classified according to the position of double bond(s) in the side chain(s) attached to the 8- and 12-positions of the alicyclic ring. Thus $PG_1$ compounds have a trans-double bond between $C_{13}$–$C_{14}$(trans-$\Delta^{13}$) and $PG_2$ compounds have a cis-double bond between $C_5$–$C_6$ and a trans-double bond between $C_{13}$–$C_{14}$(cis-$\Delta^5$, trans-$\Delta^{13}$). For example, prostaglandin $F_{1\alpha}$($PGF_{1\alpha}$) and prostaglandin $E_1$ ($PGE_1$) are characterized by the following structures IV and V.

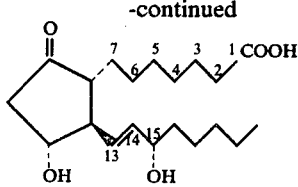
IV and

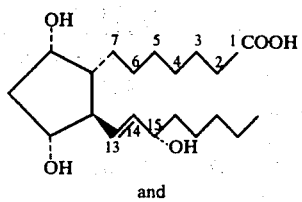
V respectively. The structures of $PGF_{2\alpha}$ and $PGE_2$, as members of the $PG_2$ group correspond to those of formulae IV and V respectively with a cis-double bond between the carbon atoms in positions 5 and 6. Compounds in which the double bond between the carbon atoms in positions 13 and 14 of members of the $PG_1$ group is replaced by ethylene are known as dihydro-prostaglandins, e.g. dihydro-prostaglandin-$F_{1\alpha}$ (dihydro-$PGF_{1\alpha}$) and dihydro-prostaglandin-$E_1$ (dihydro-$PGE_1$).

Moreover, when one or more methylene groups are added to, or eliminated from, the aliphatic group attached to the 12-position of the alicyclic ring of the prostaglandins the compounds are known, in accordance with the usual rules of organic nomenclature, as homo-prostaglandins (methylene group added) or nor-prostaglandins (methylene group eliminated), and, when more than one methylene group is added or eliminated, the number is indicated by di- tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia, $PGE_1$ inhibits blood platelet aggregation and also removes the thrombus and prevents thrombosis. PGEs and PGFs have a stimulating effect on smooth muscle and increase the intestinal peristalsis; these actions indicate therapeutic utility on post-operative ileus and as purgatives. Furthermore, PGEs and PGFs may be used as oxytocics, as abortifacients in the first and second trimesters; in the post-labour abortion of the placenta, and as oral contraceptives because they regulate the sexual cycle of female mammals. PGEs have vasodilator and diuretic activities. PGEs are useful for improvement in patients suffering from cerebral vascular disease because they increase the cerebral blood flow and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree, or hitherto unknown pharmacological properties. It has now been found that by replacing one of the hydrogen atoms attached to the ≠-position carbon atom in the aliphatic group linked to the 12-position of the alicyclic ring of prostaglandins E and F or analogues thereof by an alkylthio radical and the other hydrogen atom by an alkylthio, cycloalkylthio or phenylthio radical, the pharmacological properties of 'natural' prostaglandins may, in some aspects of their activities, be improved or modified.

The present invention accordingly provides new prostaglandin analogues of the general formula:

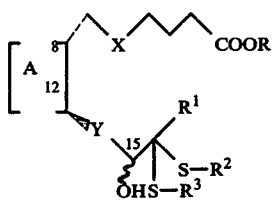
VI wherein A represents a grouping of the formula:

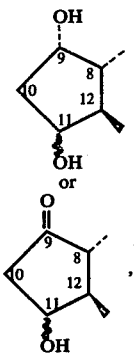
VIIA or

VIIB

X represents ethylene (i.e. —CH$_2$CH$_2$—) or, preferably, cis-vinylene (i.e. —CH=CH—), Y represents ethylene or, preferably, trans-vinylene, R represents a hydrogen atom or a straight- or branched-chain alkyl group containing from 1 to 12 carbon atoms (preferably methyl), R$^1$ represents a hydrogen atom or a straight- or branched-chain alkyl group containing from 1 to 10 (preferably 1 to 4 ) carbon atoms, R$^2$ represents a straight- or branched-chain alkyl group containing from 1 to 4 carbon atoms (preferably methyl), R$^3$ represents a straight- or branched-chain alkyl group containing from 1 to 4 carbon atoms, a cycloalkyl group containing from 4 to 7 carbon atoms, or a grouping of the general formula:

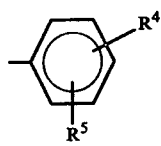
VIII wherein R$^4$ and R$^5$ each represents a hydrogen or halogen atom, a trifluoromethyl group or an alkyl group containing from 1 to 3 carbon atoms, or R$^2$ and R$^3$ together represent an ethylene or trimethylene group) and cyclodextrin clathrates of such acids and esters and, when R represents a hydrogen atom, non-toxic salts of such acids. Compounds of general formula VI wherein the hydroxy group attached to the 15-position is in the α-configuration are preferred.

The present invention is concerned with all compounds of general formula VI in the 'natural' form or its enantiomeric form, or mixtures thereof, more particularly the racemic form consisting of equimolecular mixtures of natural and its enantiomeric form.

As will be apparent to those skilled in the art, the compounds depicted in general formula VI have at least three centres of chirality, these three centres of chirality being at the alicyclic ring carbon atoms of group A identified as 8 and 12 and at the C-15 carbon atom which has attached to it a hydroxy group. Still further centres of chirality occur when the alicyclic group A carries a hydroxy group on the carbon atom in position 11 (i.e. when the ring is that of formula VIIB) or hydroxy groups in positions 9 and 11 (i.e. when the ring is that of formula VIIA) and further centres of chirality may occur in groups represented by the symbols R$^1$, R$^2$ and R$^3$. The presence of chirality leads, as is well known, to the existence of isomerism. However, the compounds of general formula VI all have such a configuration that the side-chains attached to the ring carbon atoms in the positions identified as 8 and 12 are trans with respect to each other. Accordingly, all isomers of general formula VI, and mixtures thereof, which have those side-chains attached to the ring carbon atoms in positions 8 and 12 in the trans-configuration and have a hydroxy group as depicted in the 15-position are to be considered within the scope of general formula VI.

According to a feature of the present invention, the prostaglandin analogues of general formula VI, wherein R represents a hydrogen atom or a straight- or branched-chain alkyl group containing 1 to 4 carbon atoms, preferably methyl, and the other symbols are as hereinbefore defined, are obtained by the process which comprises hydrolysing a compound of the general formula:

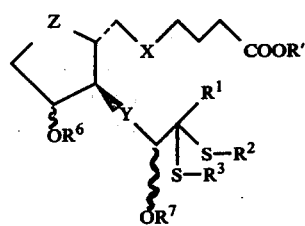
IX wherein X, Y, R$^1$, R$^2$ and R$^3$ are as hereinbefore defined, Z represents

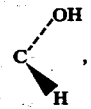

or C=O, R' represents a hydrogen atom or a straight- or branched-chain alkyl group containing 1 to 4 carbon atoms, preferably, methyl, and R$^6$ and R$^7$ each represent a 2-tetrahydropyranyl group, unsubstituted or substituted by at least one alkyl group, or a 2-tetrahydrofuranyl or 1-ethoxyethyl group, to convert the groups OR$^6$ and OR$^7$ to hydroxy groups.

The groups OR$^6$ and OR$^7$ of the compounds of general formula IX may be converted to hydroxy groups by mild hydrolysis with an aqueous solution of an organic acid, e.g. acetic acid, or with a dilute aqueous inorganic acid, e.g. hydrochloric acid, advantageously in the presence of an organic solvent miscible with water, e.g. tetrahydrofuran or an alkanol containing from 1 to 4 carbon atoms, e.g. methanol. The mild hydrolysis may be carried out at a temperature ranging from ambient to 60° C. (preferably at a temperature below 45° C.) with an acid mixture, e.g. a mixture of hydrochloric acid and water with tetrahydrofuran or methanol or a mixture of acetic acid, water and tetrahydrofuran.

Prostaglandin analogues of general formula VI wherein R represents a straight- or branched-chain alkyl group containing from 1 to 12 carbon atoms can be obtained by reaction of a prostaglandin analogue of general formula VI wherein R represents a hydrogen atom with (i) diazoalkane compounds, e.g. diazomethane, (ii) alcohols in the presence of dicyclohexylcarbodiimide as condensing agent, or (iii) alcohols following the formation of a mixed acid anhydride by adding a tertiary amine and then a pivaloyl halide or an arylsulphonyl or alkylsulphonyl halide (cf. our British Patents Nos. 1362956 and 1364125).

Compounds of general formula IX wherein Z represents C=O may be obtained from compounds of general formula IX wherein Z represents

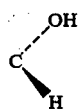

by oxidation under very mild conditions, for example by means of Collins' reagent (chromium trioxide - pyridine complex) at -20° to -50° C. or by means of dimethylsulphide - N-chlorosuccinimide at 0° to -30° C. [cf. E. J. Corey and C. U. Kim, J. Amer. Chem. Soc., 94, 7586 (1972)].

Compounds of general formula IX wherein Z represents

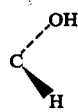

and R' represents a hydrogen atom may be prepared by reacting a compound of the general formula:

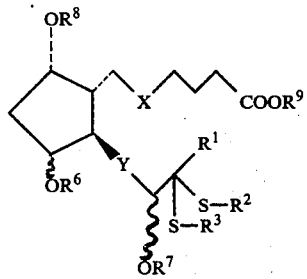

(wherein X, Y, $R^1$, $R^2$, $R^3$, $R^6$ and $R^7$ are as hereinbefore defined, $R^8$ represents an alkylcarbonyl group containing from 2 to 5 carbon atoms, and $R^9$ represents a straight- or branched-chain alkyl group containing from 1 to 4 carbon atoms) with an aqueous solution of an alkali metal, e.g. sodium or potassium, hydroxide or carbonate in the presence of a water miscible organic solvent, e.g. tetrahydrofuran or an alkanol containing from 1 to 4 carbon atoms.

Compounds of general formula IX wherein Z represents

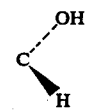

and R' represents a straight- or branched-chain alkyl group containing 1 to 4 carbon atoms may be prepared by reacting a compound of general formula X with anhydrous potassium carbonate in an anhydrous alkanol containing 1 to 4 carbon atoms in a straight- or branched-chain, preferably absolute methanol.

Compounds of general formula X may be prepared by reacting a compound of the general formula:

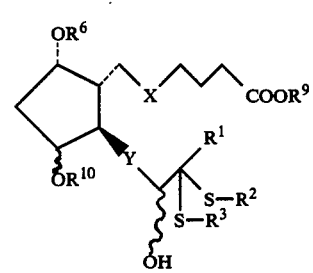

(wherein X, Y, $R^1$, $R^2$, $R^3$, $R^8$ and $R^9$ are as hereinbefore defined and $R^{10}$ represents a hydrogen atom or the group $R^6$ as hereinbefore defined) with a dihydropyran, dihydrofuran or ethyl vinyl ether in an inert organic solvent, e.g. methylene chloride, in the presence of a condensing agent, e.g. p-toluenesulphonic acid.

Compounds of general formula XI wherein $R^{10}$ represents a hydrogen atom, i.e. compounds of general formula XIA;

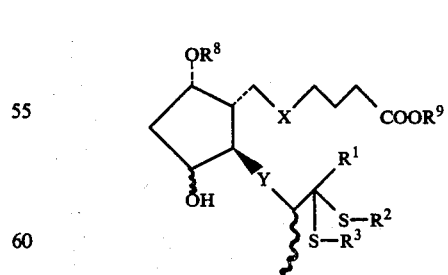

wherein X, Y, $R^1$, $R^2$, $R^3$, $R^8$ and $R^9$ are as hereinbefore defined may be prepared by hydrolysing compounds of general formula XI wherein $R^{10}$ represents the group $R^6$, i.e. compounds of general formula XIB:

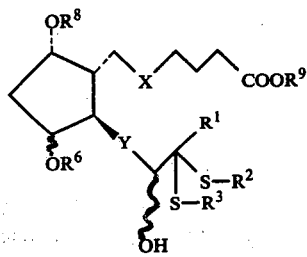

XIB (wherein X, Y, $R^1$, $R^2$, $R^3$, $R^6$, $R^8$ and $R^9$ are hereinbefore defined) by the methods as hereinbefore described for the conversion of a compound of general formula IX to a compound of general formula VI.

Compounds of general formula XIB may be prepared by the reaction of a compound of the general formula:

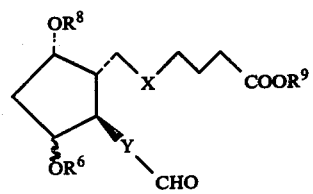

XII (wherein X, Y, $R^6$, $R^8$ and $R^9$ are as hereinbefore defined) with an organolithium compound of the general formula:

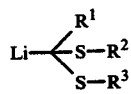

XIII (wherein $R^1$, $R^2$ and $R^3$ are as hereinbefore defined). The reaction is preferably effected at a low temperature, preferably below -30° C., in an inert organic solvent, e.g. diethyl ether, tetrahydrofuran, n-hexane or 1,2-dimethoxyethane, for 10 to 60 minutes. The reaction mixture is then hydrolysed by treatment with water or an aqueous solution of an acid or ammonium chloride to give a mixture of the α- and β-hydroxy epimers of compounds of general formula XIB. It is sometimes possible to separate the isomer having the hydroxy group in α-configuration from the isomer having the hydroxy group in β-configuration by column chromatography of the mixture using silica gel. It is sometimes easier to separate the isomer having the hydroxy group in α-configuration of general formulae XIA and VI from the corresponding isomer having the hydroxy group in β-configuration by column chromatography on silica gel than to separate the isomers of general formula XIB.

According to a further feature of the present invention, compounds of general formula XIA may be directly converted to compounds of the general formula VI wherein A represents a grouping of formula VIIA, R represents a hydrogen atom, and the other symbols are as hereinbefore defined by hydrolysis under alkaline conditions. The hydrolysis is preferably carried out with an aqueous solution of an alkali metal, e.g. sodium or potassium, hydroxide or carbonate in the presence of a water miscible organic solvent, e.g. tetrahydrofuran or an alkanol containing from 1 to 4 carbon atoms.

Compounds of general formula VI wherein Y represents an ethylene group, i.e. compounds of the general formula:

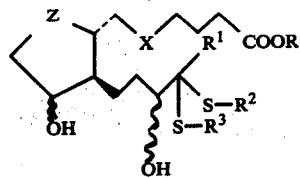

VIA (wherein X, Z, $R^1$, $R^2$, $R^3$ and R are as hereinbefore defined), may be converted to compounds of the general formula:

XIV (wherein X, Z, $R^1$ and R are as hereinbefore defined) by reaction with N-chlorosuccinimide and silver nitrate in an inert solvent, e.g. water or acetonitrile, at 0° C. to room temperature for 20 to 60 minutes.

The compounds of general formula XII wherein X represents cis-vinylene, Y represents trans-vinylene and $R^6$, $R^8$ and $R^9$ are as hereinbefore defined, hereafter depicted by general formula XIIa, are prepared by the sequences of reactions hereinafter depicted schematically in Chart A.

CHART A

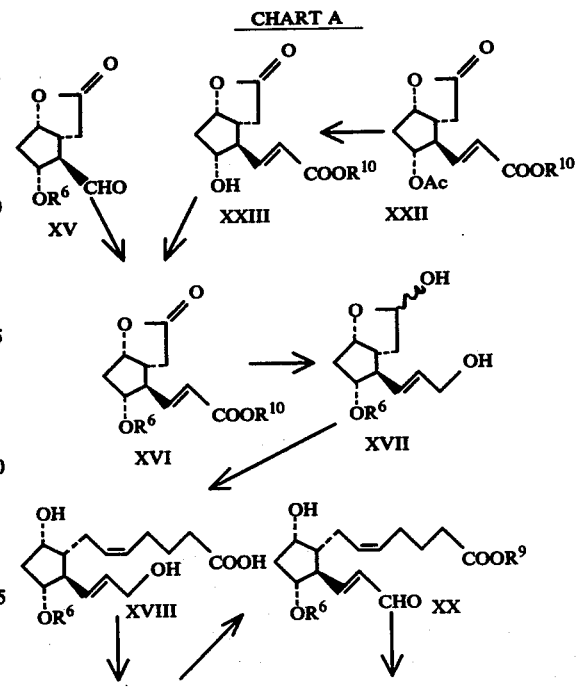

-continued
CHART A

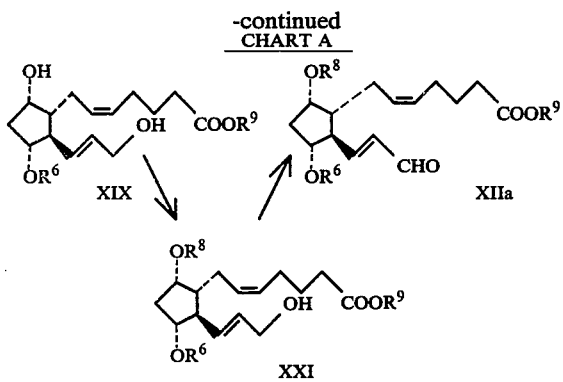

wherein $R^{10}$ represents a straight- or branched-chain alkyl group containing 1 to 4 carbon atoms, and $R^6$, $R^8$ and $R^9$ are as hereinbefore defined.

Referring to Chart A, the starting compounds of general formula XV may be prepared from the compounds of general formula XXIV hereafter by the series of reactions depicted schematically below in Chart B, wherein $R^6$ is as hereinbefore defined.

CHART B

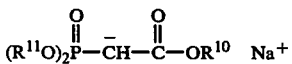

Compounds of general formula XXV may be prepared from compounds of general formula XXIV by catalytic reduction in the presence of a hydrogenation catalyst, for example palladium on charcoal or palladium black, and converted to compounds of general formula XV by oxidation under mild conditions, e.g. with Collins' reagent and at a moderately low temperature.

Compounds of general formula XV may be transformed stereospecifically to trans-α, β-unsaturated esters of general formula XVI by reaction with the sodio derivative of compounds of general formula:

$$(R^{11}O)_2\overset{O}{\overset{\|}{P}}-CH^--\overset{O}{\overset{\|}{C}}-OR^{10} \quad Na^+ \qquad XXVI$$

(wherein $R^{10}$ is as hereinbefore defined and $R^{11}$ represents an alkyl group containing from 1 to 4 carbon atoms) in an inert organic solvent, e.g. tetrahydrofuran or 1,2-dimethoxyethane, at a temperature of 0° C. to 30° C. for 2 hours, in a high yield, e.g. 70% to 90%.

Compounds of general formula XVI may be converted quantitatively to compounds of general formula XVII by reduction with more than three molar equivalents of diisobutylaluminium hydride in an inert solvent, e.g. toluene, n-pentane or n-hexane, at a low temperature, e.g. -78° C. to -20° C.

Compounds of general formula XVIII may be prepared by the reaction of a compound of general formula XVII with a compound of formula:

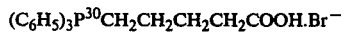

XXVII in the presence of a strong base, for example sodium methylsulphinylmethylide, under the normal conditions utilized for effecting the Wittig reaction, e.g. in an inert solvent at ambient temperature. The reaction is preferably carried out in dimethyl sulphoxide because the compound of general formula XXVII is practically insoluble in other solvents, e.g. tetrahydrofuran, and because a cis-double bond must be formed stereospecifically in the Wittig reaction. For the better performance of the Wittig reaction, more than three equivalents of the phosphorane compound, prepared from the compound of general formula XXVII, are required. Reaction between the compounds of general formula XVII and the phosphorane is usually completed in about one to five hours at laboratory temperature. The product of formula XVIII, i.e. the acid component of the reaction mixture, may be isolated from the reaction mixture in a high yield by conventional procedures.

Compounds of general formula XVIII may be esterified to obtain compounds of general formula XIX by reaction with (a) appropriate diazoalkane compounds, e.g diazomethane, (b) appropriate alcohols in the presence of dicyclohexyl carbodiimide as condensing agent, or (c) appropriate alcohols following the formation of a mixed acid anhydride by adding a tertiary amine and then a pivaloyl halide or an arylsulphonyl or alkylsulphonyl halide (cf. our British Pats. Nos. 1362956 and 1364125), and then, if desired, converted to compounds of general formula XXI by reaction with trimethylchlorosilane in an inert organic solvent, for example methylene chloride, in the presence of a base, for example pyridine or a tertiary amine, at a low temperature, e.g. at a temperature of -30° C. to 0° C., then reacting the resulting trimethylsilyl ether with the appropriate acyl halide or acid anhydride in an inert organic solvent, for example methylene chloride, in the presence of a base, for example pyridine or a tertiary amine, at a low temperature, e.g. at a temperature of 0° C. to 30° C., and treating the resulting acyl ether by methods known per se for the removal of the trimethylsilyl group, for example by treatment with an acid; it is preferable not to use a strong acid in order to avoid the risk of the removal of the group $R^6$. By the term "methods known per se" as used in this specification is meant methods heretofore used or described in the chemical literature.

Compounds of general formula XXI may be converted to compounds of general formula XIIa by oxidation with manganese dioxide, for example in an inert solvent, e.g. methylene chloride, at laboratory temperature, which oxidizes an allylic alcohol group selectively.

Compounds of general formula XIIa can be prepared from compounds of general formula XIX by oxidation with manganese dioxide, for example in an inert organic solvent, e.g. methylene chloride, at laboratory temperature, and then acylation via compounds of general formula XX.

Compounds of general formula XVI can also be prepared from compounds of general formula XXII by selective deacetylation with an equimolar amount of anhydrous potassium carbonate in absolute methanol and then etherification with a dihydropyran, dihydrofuran or ethylvinyl ether in an inert organic solvent, such as methylene chloride, in the presence of a condensing agent, for example p-toluenesulphonic acid.

Compounds of general formula XXIV may be prepared by known methods, for example as described in J. Org. chem., 37, 2921 (1972) for the preparation of the compound of general formula XXIV wherein $R^6$ is a 2-tetrahydropyranyl group.

Compounds of general formula XII wherein X represents cis-vinylene or ethylene and Y represents trans-vinylene may also be obtained by reaction of a compound of the general formula:

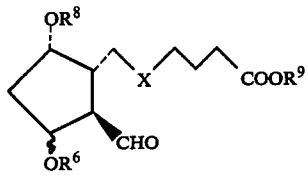

XXVIII (wherein X, $R^6$, $R^8$ and $R^9$ are as hereinbefore defined) with formylmethylenetriphenylphosphorane in an inert solvent, for example benzene, at about 70° C. for several hours, for example 20 hours, to give compounds of the general formula:

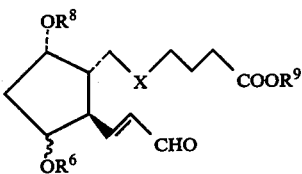

XIIb wherein X, $R^6$, $R^8$ and $R^9$ are as hereinbefore defined.

Compounds of general formula XII wherein X and Y represent —CH$_2$CH$_2$- may be obtained by reduction of compounds of general formula XIIa or of general formula XIIb wherein X represents ethylene by means of diimide, which is prepared from hydrazine and an oxidizing agent, for example hydroperoxide (cf. J. Chem. Ed. 42, 254 (1965)). Compounds of general formula XII wherein X represents cis—CH=CH— and Y represents —CH$_2$CH$_2$—may be obtained by the selective reduction of the carbonyl conjugated double bond Y of compounds of general formula XIIa by methods known per se, for example by means of lithium 1-pentyne-hydrocuprate (LiCuH—CCC$_3$H$_7$) (see J. Amer. Chem. Soc. 96, 3686 (1974)).

The compounds of general formula XXVIII wherein X, $R^6$, $R^8$ and $R^9$ are as hereinbefore defined and the group OR$^6$ is in α-configuration [hereinafter depicted in general formula XXVIIIA], used as starting materials in the hereinbefore described procedure, may themselves be prepared by methods known per se from compounds of general formula XXIX by the series of reactions depicted schematically below in Chart C:

CHART C

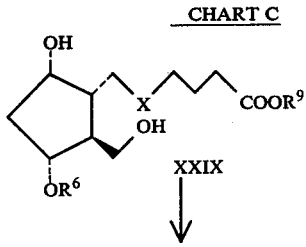

XXIX

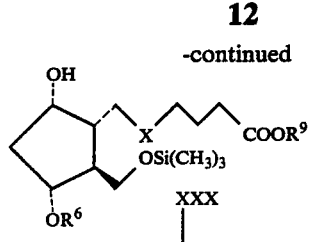

XXX

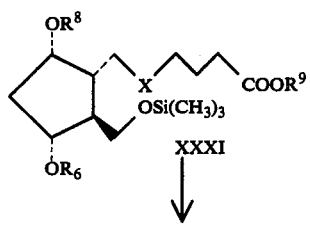

XXXI

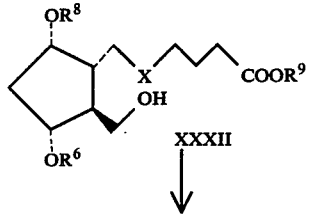

XXXII

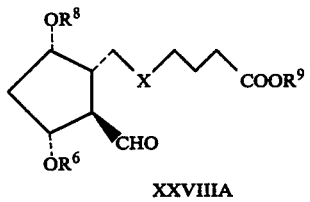

XXVIIIA wherein X, $R^6$, $R^8$ and $R^9$ are as hereinbefore defined, and preferably $R^8$ represents an acetyl group.

Compounds of formula XXX may be prepared by reacting a compound of formula XXIX with trimethylchlorosilane in an inert organic solvent, for example methylene chloride, in the presence of a base, for example pyridine or a tertiary amine, at a low temperature, e.g. at a temperature of -30° C. to 0° C. Compounds of formula XXXI may be prepared by reacting a trimethylsilyl ether of formula XXX with the appropriate acyl chloride or acid anhydride in an inert organic solvent, for example methylene chloride, in the presence of a base, for example pyridine or a tertiary amine, at a low temperature, e.g. at a temperature of 0° C. to 30° C. Compounds of formula XXXII may be prepared by treating a compound of formula XXXI by methods known per se for the removal of the trimethylsilyl group, for example by treatment with an acid; it is preferable not to use a strong acid in order to avoid the risk of the removal of the group $R^6$. The compounds of formula XXXII may be converted to compounds of formula XXVIIIA under mild and neutral conditions, e.g. with chromium trioxide-pyridine complex or Jones' reagent and at a moderately low temperature.

The compounds of general formula XXIX may themselves be prepared by the method described in Japanese Patent Application No. 48-17416 from the known compounds of formula XXXIII below [the racemic form of the compound of formula XXXIII is described in J. Amer. Chem. Soc. 91, 5675 (1969) and the natural configuration compound of formula XXXIII is described in J. Amer. Chem. Soc. 92, 397 (1970)]which may be represented by the series of reactions depicted schematically below in Chart D:-

CHART D

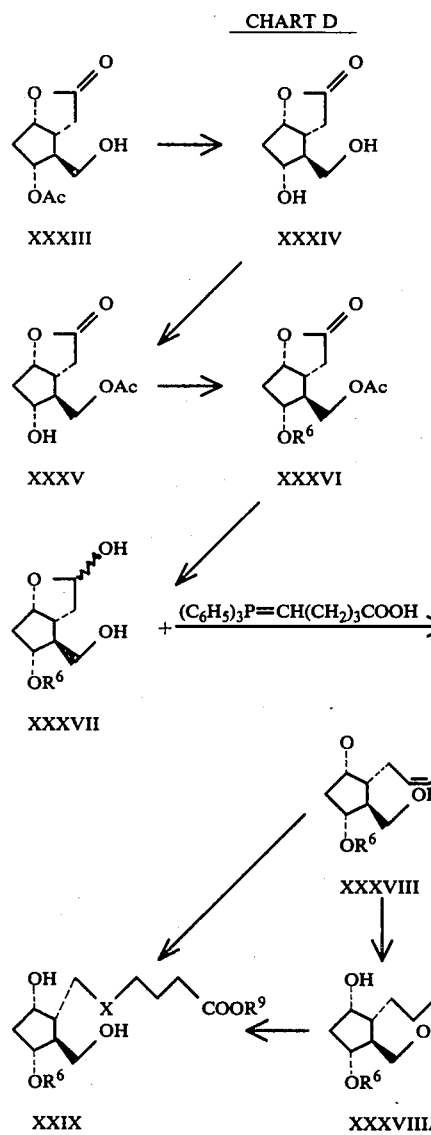

XXXIII

XXXIV

XXXV

XXXVI

XXXVII

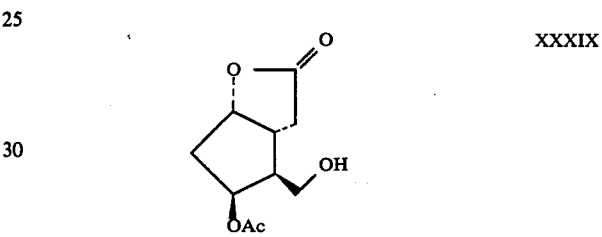

XXXVIII

XXIX

XXXVIIIA wherein $R^6$ and $R^9$ are as hereinbefore defined and Ac represents the acetyl group (—COCH$_3$).

Compounds of formula XXXIV may be prepared by hydrolysis under alkaline conditions of compounds of formula XXXIII. Compounds of formula XXXV may be obtained by the acetylation of compounds of formula XXXIV under mild conditions and may be converted into compounds of formula XXXVI by reaction with a dihydropyran, dihydrofuran or ethyl vinyl ether in an inert solvent, e.g. methylene chloride, in the presence of a condensing agent, e.g. p-toluenesulphonic acid. Compounds of formula XXXVII may be prepared by reducing compounds of formula XXXVI with diisobutylaluminium hydride in toluene for about 15 minutes at -60° C. Dimsyl anion, previously prepared from sodium hydride and dimethyl sulphoxide is reacted with 4-carboxy-n-butyl-triphenylphosphonium bromide to form 4-carboxy-n-butylidenetriphenylphosphorane. To that compound is added a compound of formula XXXVII and the mixture in dimethyl sulphoxide is made to react for 2 hours at room temperature to yield a compound of formula XXXVIII.

Compounds of formula XXXVIII may, if desired, be reduced to give compounds of formula XXXVIIIA. Suitably, the reduction may be effected by hydrogenation in the presence of a hydrogenation catalyst, for example palladium on charcoal, palladium black or platinum dioxide, in the presence of an inert organic solvent, for example a lower alkanol, e.g. methanol or ethanol, at laboratory temperature at normal or elevated pressure, e.g. at a hydrogen pressure from atmospheric to 15 kilogrammes per square centimeter. Compounds of formulae XXXVIII or XXXVIIIA are then reacted with a diazoalkane in a suitable inert solvent, e.g. diethyl ether, to give compounds of formula XXIX.

The compounds of general formula XXVIII wherein X represents cis-vinylene, $R^6$, $R^8$ and $R^9$ are as hereinbefore defined and the group $OR^6$ is in β-configuration, which may be used as starting materials in the hereinbefore described procedures, may themselves be prepared by the series of reaction depicted in Charts C and D but replacing the compounds of formula XXXIII by compounds of the formula:

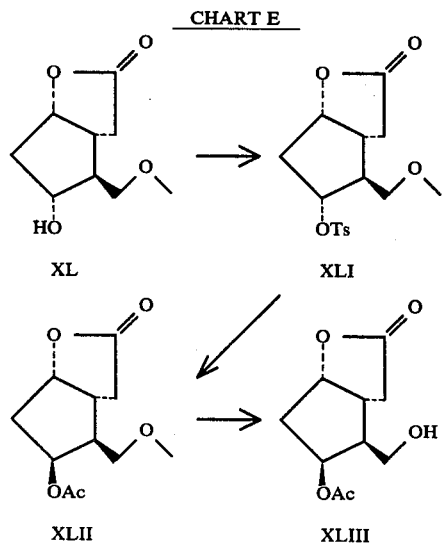

XXXIX

, wherein Ac is as hereinbefore defined.

A method for the preparation of the bicyclo- octane starting materials of formula XXXIX, wherein Ac is as hereinbefore defined, utilizing known procedures may be represented by the series of reactions depicted schematically below in Chart E (cf. E. J. Corney and Shiro Terashima, Tetrahedron Letters, No. 2, pp. 111–113, 1972):

CHART E

XL

XLI

XLII

XLIII wherein Ac is as hereinbefore defined and Ts represents the tosyl group. The various reactions depicted above in Chart E may be effected by methods known per se.

Compounds of formula XLII may be prepared by reacting compounds of formula XLI with tetraethylammonium acetate.

The prostaglandin analogues of general formula VI wherein R represents a hydrogen atom may, if desired, be converted by methods known per se into salts.

The salts may be prepared, for example, by reaction of stoichiometric quantities of an acid of general formula VI and the appropriate base, e.g. an alakli metal hydroxide or carbonate, ammonium hydroxide or carbonate, ammonia or an amine, in a suitable solvent. The salts may be isolated by lyophilisation of the solution or, if sufficiently insoluble in the reaction medium, by filtration, if necessary after removal of part of the solvent. Preferably the salts are non-toxic salts, i.e. salts the cations of which are relatively innocuous to the animal organism when used in therapeutic doses so that the beneficial pharmacological properties of the prostaglandins of general formula VI are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The prostaglandins of general formula VI may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70° C. during the preparation of the cyclodextrin clathrates. $\alpha$, $\beta$-or $\gamma$-Cyclodextrins or mixtures thereof may be used in the preparation of the cyclodextrin clathrates. Conversion into their cyclodextrin clathrates serves to increase the stability of the prostaglandin compounds.

The prostaglandin analogues of general formula VI and their cyclodextrin clathrates and, when R in general formula VI represents a hydrogen atom, their non-toxic salts, possess the valuable pharmacological properties typical of prostaglandins, in a selective fashion, including, in particular, inhibitory activity on gastric acid secretion and gastric ulceration, abortifacient activity and stimulatory activity on uterine contraction, luteolytic activity and antinidatory activity and bronchodilator activity at doses which do not, in general, induce diarrhoea as an undesired side-effect, and are useful in the treatment of gastric ulceration, in the termination of pregnancy and induction of labour in pregnant female mammals, in the control of oestrus in female mammals and in the prevention of pregnancy in female mammals, and in the treatment of asthma. For example, in standard laboratory screening tests, (1) in rats in which gastric ulceration was induced by stress according to the method of Takagi and Okabe [Jap. J. Pharmac., 18, 9–18 (1968)], oral administration of 16($\xi$)-phenylthio-16-methylthio-17,18,19,20-tetranor-PGE$_2$ methyl ester produces 80.34% and 80.09% inhibitions, respectively, of stress ulceration at doses of 100 and 200 $\mu$g./kg. animal body weight, respectively, while oral administration of 16($\xi$)-phenylthio-16-methylthio-17,18,19,20-tetranor-PGE$_1$ methyl ester produces 57.34% and 85.32% inhibitions, respectively, of stress ulceration at doses of 100 and 200 $\mu$g./kg. animal body weight, respectively; (2) when perfused into the stomach of the pentagastrin-treated rat, 16,16-(1,3-dithiapentano)-PGE$_2$ methyl ester and 16($\xi$)-phenylthio-16-methylthio-17,18,19,20-tetranor-PGE$_1$ methyl ester produce increases in gastric acid pH from 2.0–2.5 to at least 4.0 in two out of five animals when administered at doses of 10 $\mu$g./animal/minute and 0.5–1.0 $\mu$g./animal/minute, respectively, and 16($\xi$)-phenylthio-16-methylthio-17,18,19,20-tetranor-PGE$_2$ methyl ester produces an increase in gastric acid pH from 2.0–2.5 to at least 4.0 in 50% of pentagastrin-treated rats when administered at a dose of 0.9 (confidence limit 0.54–1.50) $\mu$g./animal/minute; (3) when administered intravenously on the 20th day of pregnancy, 16($\xi$)-phenylthio-16-methylthio-17,18,19,20-tetranor-PGF$_{2\alpha}$, 15-[2-(1,3-dithiacyclohexyl)]-16,17,18,19,20-pentanor-PGF$_{2\alpha}$, 16,16-(1,5-dithiapentano)-PGF$_{2\alpha}$ methyl ester and 16($\xi$)-phenylthio-16-methylthio-17,18,19,20-tetranor-PGE$_1$ methyl ester stimulate uterine contraction in the pregnant female rat at doses of 5.0–10.0, 10.0–20.0, 20.0–50.0 and 0.5–1 $\mu$g./kg. animal body weight, respectively; (4) by subcutaneous administration on the 3rd, 4th and 5th days of pregnancy, 16($\xi$)-phenylthio-16-methylthio-17,18,19,20-tetranor-PGF$_{2\alpha}$, 16,16-(1,5-dithiapentano)-PGF$_{2\alpha}$methyl ester and 15-[2-(1,3-dithiacyclohexyl)]-16,17,18,19,20-pentanor-PGF$_{2\alpha}$inhibit implantation in pregnant female rats when administered at daily doses of 1.0, 2.0 and 2.0 mg./kg. animal body weight, respectively; (5) when administered intraperitoneally on the 17th day of gestation, 16($\xi$)-phenylthio-16-methylthio-17,18,19,20-tetranor-PGE$_2$ methyl ester induces abortion in pregnant female rats when administered twice at a dose of 1.0 mg./kg. animal body weight; (6) after intravenous administration in the anaesthetized guinea pig in which increases in resistance in the respiratory tract were induced by the administration of histamine, as determined by the method of Konzett and Rossler [Arch. exp. Path. Pharmak., 195, 71–74, (1940)], 16,16-(1,3-dithiapentano)-PGE$_2$ methyl ester produces inhibitions of the histamine induced bronchoconstriction of 35.9% and 22.9%, respectively, at doses of 10.0 and 30.0 $\mu$g./kg. animal body weight, respectively, and (7) by inhalation in an aerosol, convulsions induced by the inhalation of a histamine-containing aerosol in the conscious guinea pig are delayed by 16,16-(1,3-dithiapentano)-PGE$_2$ methyl ester leading to increases in the preconvulsion time of 57%, 11% and 11%, respectively, at doses of 10.0, 100 and 300 $\mu$g./ml. of aerosol, respectively, while (8), the doses of 15-[2-(1,3-dithiacyclohexyl)]-16,17,18,19,20-pentanor-PGE$_2$ methyl ester, 16,16-(1,5-dithiapentano)-PGE$_2$ methyl ester, 16($\xi$)-phenylthio-16-methylthio-17,18,19,20-tetranor-PGE$_2$ ester and 16($\xi$)-phenylthio-16-methylthio-17,18,19,20-tetranor-PGE$_1$ methyl ester required to produce diarrhoea in 50% of mice (ED$_{50}$) by oral administration are 8.9, 3.2, 1.43 and 1.2 mg./kg. animal body weight, respectively. The prostaglandin analogues of general formula XIV also possess the valuable pharmacological properties typical of prostaglandins, in a selective fashion, including, in particular, hypotensive and bronchodilator activity at doses which do not, in general, induce diarrhoea as undesired side-effect, and are useful in the treatment of hypertension and asthma. For example, in standard laboratory screening tests, 16-oxo-13,14-dihydro-15(ξ)-PGE$_1$ methyl ester (1) by intravenous administration to the allobarbital-anaesthetized dog, produces falls in blood pressure of 18 mm.Hg and 42 mm.Hg, respectively, lasting 12 minutes and 19 minutes, respectively, at doses of 0.5 and 1.0 μg./kg. animal body weight, respectively; (2) by intravenous administration in the anaesthetized guinea-pig in which increases in resistance in the respiratory tract were induced by the administration of histamine, as determined by the method of Konzett and Rossler [Arch. exp. Path. Pharmak., 195, 71–74 (1940)], produces inhibitions of the histamine induced bronchoconstriction of 23.5%, 68.5% and 84.0%, respectively, at doses of 0.1, 0.5 and 1.0 μg./kg. animal body weight, respectively, while (3), the dose required to produce diarrhoea in 50% of mice (ED$_{50}$) by oral administration is 8.1 mg./kg. animal body weight.

Preferred compounds of the invention are those compounds of general formula VI wherein R represents a hydrogen atom or a methyl group, $R^1$ represents a hydrogen atom or an alkyl group containing from 1 to 4 carbon atoms, and $R^2$ represents an alkyl group containing from 1 to 4 carbon atoms and $R^3$ represents a phenyl group or $R^2$ and $R^3$ together represent an ethylene or trimethylene group.

The following Reference Examples and Examples illustrate the process of the present invention and products thereof. In the Examples 'IR', 'NMR' and 'TLC' represent respectively 'Infrared absorption spectrum', 'Nuclear magnetic resonance spectrum' and 'Thin layer chromatography'. Solvent ratios for chromatographic separations are by volume.

REFERENCE EXAMPLE 1

Phenylthio-methylthio-methane 120 ml. of a 1.3M n-butyllithium solution in n-hexane were added dropwise to a solution of 18.8 ml. of thioanisole in 240 ml. of tetrahydrofuran at −20° C. and the reaction mixture was stirred at that temperature for 2 hours. After cooling to −70° C., 16.4 g. of dimethyldisulphide were added to the reaction mixture, which was then stirred at −70° C. for 15 minutes and at room temperature for 1 hour. The reaction mixture was poured into dilute aqueous hydrochloric acid and extracted with ethyl acetate. The extracts were washed with water and an aqueous solution of sodium chloride and concentrated under reduced pressure. The residue was purified by distillation in vacuo to give 18.0 g. of the title compound having the following physical characteristics:
b.p.: 98 to 102° C./3 mmHg;
IR (liquid film):ν; 2900, 1590, 1200, 750 cm$^{-1}$;
NMR (CCl$_4$ solution):δ; 7.65–7.10 (5H, m), 3.92 (2H, s), 2.20 (3H, s);
Refractive index: $n_D^{20}$ = 1.6074;
Mass spectrum: m/e; 170 (M$^+$).

REFERENCE EXAMPLE 2

2-Oxa-3-oxo-6-syn-(2-methoxycarbonyl-trans-vinyl)-7-anti-acetoxy-cis-bicyclo[3,3,0]octane Under an atmosphere of nitrogen and at laboratory temperature, 140 ml. of absolute methylene chloride and 16.1 ml. of absolute pyridine was stirred with 10 g. of chromium trioxide for 30 minutes. 20 g. of infusorial earth were then added to the solution. After cooling the temperature to 0° C., 2.14 g. of 2-oxa-3-oxo-6-syn-hydroxymethyl-7-anti-acetoxy-cis-bicyclo[3,3,0]octane [prepared as described in J. Amer. Chem. Soc., 92, 397 (970)] in 20 ml. of methylene chloride were then added and the mixture stirred for 15 minutes at 0° C. The reaction mixture was then treated with 25 g. of sodium bisulphate and stirred for a further 10 minutes at 0° C. and filtered through a pad of magnesium sulphate. The filtrate was then concentrated under reduced pressure and below 0° C. to give 2-oxo-3-oxo-6-syn-formyl-7-antiacetoxy-cis-bicyclo[3,3,0]octane.

369 mg. of sodium hydride (65% content) were suspended in 60 ml. of absolute tetrahydrofuran. With stirring under an atmosphere of nitrogen at room temperature, 1.82 g. of trimethyl phosphonoacetate [prepared as described in C.R. Acad. Sci. Paris. Ser. A, B 262B, 515 (1966)] were added to the suspension, and stirred for 30 minutes.

The formyl compound, obtained above, in 30 ml. of tetrahydrofuran, was added, whilst maintaining the temperature below 15° C., and stirred for 2 hours at 15° C. Then the reaction mixture was treated with 2 ml. of acetic acid to pH 5 and concentrated slightly. The product was treated with 20 ml. of water and extracted twice with 80 ml. of ethyl acetate (total volume 160 ml.). The organic layer was washed with an aqueous solution of sodium chloride, dried over magnesium sulphate and concentrated under reduced pressure. The residue was purified by column chromatography on silica gel using a mixture of ethyl acetate - benzene (1:4) as eluent to give 2.0 g. of the title compound having the following physical characteristics:
IR (liquid film): ν; 2970, 1775, 1735, 1710, 1650, 1240, 1160, 1037 and 980 cm$^{-1}$;
NMR (CDCl$_3$ solution):δ; 6.77 (1H, d), 5.87 (1H, d), 5.00 (2H, m), 3.70 (3H, s), 3.0–1.9 (6H, m), 2.04 (3H, s);
TLC (developing solvent, ethyl acetate - benzene = 1:2); Rf 32 0.38.

REFERENCE EXAMPLE 3

2-Oxa-3-oxo-6-syn-(2-methoxycarbonyl-trans-vinyl)-7-anti-hydroxy-cis-bicyclo[3,3,0]octane 2.68 g. of 2-oxa-3-oxo-6-syn-(2-methoxycarbonyl-trans-vinyl)-7-anti-acetoxy-cis-bicyclo[3,3,0]octane (prepared as described in Reference Example 2) in 30 ml. of absolute methanol and 1.38 g. of potassium carbonate were stirred at room temperature for 15 minutes, successively cooled in an ice-bath and neutralized with 20 ml. of 1N hydrochloric acid. 260 ml. of ethyl acetate and 27 ml. of an aqueous solution of sodium bicarbonate were added to the reaction mixture and separated into two layers. The organic layer was washed with an aqueous solution of sodium chloride, dried over magnesium sulphate and concentrated under reduced pressure to give 1.96 g. of the title compound having the following physical characteristics:
IR (liquid film):ν; 3430, 1786–1690 (broad) and 1650 cm$^{-1}$;
NMR (CDCl$_3$ solution);δ; 6.82 (1H, dd), 5.90 (1H, d), 4.95 (1H, m), 3.72 (3H, s), 4.30–3.25 (2H, m) and 2.90–1.70 (6H, m);
TLC (developing solvent, methylene chloride - methanol = 19:1); Rf = 0.38.

REFERENCE EXAMPLE 4

2-Oxa-3-oxo-6-syn-(2-methoxycarbonyl-trans-vinyl)-7-anti-(2-tetrahydropyranyloxy)-cis-bicyclo[3,3,0]octane 2.31 g. of 2-oxa-3-oxo-6-syn-(2-methoxycarbonyl-trans-vinyl)-7-anti-hydroxy-cis-bicyclo[3,3,0]octane (prepared as described in reference Example 3) were dissolved in 30 ml. of methylene chloride and stirred with 20 ml. of p-toluenesulphonic acid and 3 ml. of dihydropyran for 15 minutes at room temperature. The reaction mixture was neutralized with an aqueous solution of sodium bicarbonate, diluted with ethyl acetate, washed with an aqueous solution of sodium chloride, dried over magnesium sulphate and concentrated under reduced pressure. The residue was purified by column chromatography on silica gel using a mixture of ethyl acetate - benzene (1:3) as eluent to give 3.0 g. of the title compound as white crystals having the following physical characteristics:

m.p. : 85° C.;
IR (KBr tablet):$\nu$; 2930, 1770, 1650, 1343, 1240 and 1152 $cm^{-1}$;
NMR (CDCl$_3$ solution):$\delta$; 6.78 (1H, dd), 5.84 (1H, d), 4.97 (1H, m), 4.63 (1H, m), 3.71 (3H, s) and 4.30–3.20 (3H, m);
TLC (developing solvent, ethyl acetate - benzene = 1:2); Rf = 0.34.

REFERENCE EXAMPLE 5

2-Oxa-3-hydroxy-6-syn-(3-hydroxyprop-trans-1-enyl)-7-anti-(2-tetrahydropyranyloxy)-cis-bicyclo[3,3,0]octane 3.10 g. of 2-oxa-3-oxo-6-syn-(2-methoxycarbonyl-trans-vinyl)-7-anti-(2-tetrahydropyranyloxy)-cis-bicyclo[3,3,0]octane (prepared as described in Reference Example 4) were dissolved in 100 ml. of toluene and cooled to −65° C. To the solution, 23 ml. of a 25(w/v)% solution of diisobutylaluminium hydride in toluene were added and stirred for 20 minutes at −60° C. Methanol was then added to decompose excess diisobutylaluminium hydride together with water. The precipitate was filtered off and the filtrate was dried and concentrated under reduced pressure to give 2.8 g. of the title compound having the following physical characteristics:

IR (liquid film):$\nu$; 3390, 2930, 1350 and 1120 $cm^{-1}$;
NMR (CDCl$_3$ solution):$\delta$; 5.75–5.15 (3H, m) and 4.75–3.34 (8H, m);
TLC (developing solvent, methylene chloride - methanol = 19:1); Rf = 0.23.

REFERENCE EXAMPLE 6

2$\alpha$-(6-Methoxycarbonylhex-cis-2-enyl)-3$\beta$-(3-hydroxyprop-trans-1-enyl)-4$\alpha$-(2-tetrahydropyranyloxy)-cyclopentan-1$\alpha$-ol 2.94 g. of sodium hydride (65% content) were suspended in 40 ml. of dimethyl sulphoxide and stirred with heating at 65° C. for 40 minutes to obtain sodium methyl sulphinylmethylide. The reaction mixture was allowed to cool to room temperature and then added dropwise to a solution of 18.5 g. of (4-carboxybutyl)triphenylphosphonium bromide in 40 ml. of dimethyl sulphoxide, the reaction temperature being kept within the range of 20° C. to 25° C.

A solution of 2.84 g. of 2-oxa-3-hydroxy-6-syn-(3-hydroxy-prop-trans-1-enyl)-7-anti-(2-tetrahydropyranyl-oxy)-cis-bicyclo[3,3,0]octane (prepared as described in Reference Example 5) in 40 ml. of dimethyl sulphoxide was added, and the mixture stirred vigorously at 25° C. for 1 hour. The reaction mixture was poured into 500 ml. of ice-water and neutral substances were removed by extraction with a mixture of ethyl acetate and diethyl ether (1:1). The aqueous layer was acidified to pH 3 with a saturated solution of oxalic acid and extracted with a mixture of diethyl ether and ethyl acetate (1:1). The extracts, after washing with water, were dried over magnesium sulphate and concentrated under reduced presure to give crude 2$\alpha$-(6-carboxyhex-cis-2-enyl)-3$\beta$-(3-hydroxyprop-trans-1-enyl)-4$\alpha$-(2-tetrahydropyranyloxy)-cyclopentan-1$\alpha$-ol having the following physical characteristics:

IR (liquid film):$\nu$; 2930, 1720, 1240 and 1120 $cm^{-1}$;
NMR (CDCl$_3$ solution):$\delta$; 5.70–5.25 (4H, m) and 4.62 (1H, m);
TLC (developing solvent, methylene chloride - methanol = 19:1); Rf = 0.23.

The crude 6-carboxy compound thus obtained was dissolved in 40 ml. of methylene chloride, cooled to 0° C. nd a solution of diazomethane in diethyl ether was added until the reaction mixture was coloured pale yellow. The reaction mixture was then concentrated under reduced pressure and the residue was subjected to column chromatography on silica gel using a mixture of ethyl acetate - cyclohexane (1:1) as eluent to give 2.87 g. of the title compound having the following physical characteristics:

IR (liquid film):$\nu$; 3420, 2930, 1740, 1435 and 1020 $cm^{-1}$;
NMR (CDCl$_3$ solution):$\delta$; 5.75–5.20 (4H, m), 4.67 (1H, m), 4.20–3.30 (6H, m) and 3.67 (3H, s);
TLC (developing solvent, ethyl acetate - cyclohexane = 2:1); Rf = 0.31.

REFERENCE EXAMPLE 7

2$\alpha$-(6-Methoxycarbonylhex-cis-2-enyl)-3$\beta$-(2-formyl-trans-vinyl)-4$\alpha$-(2-tetrahydropyranyloxy)-cyclopentan-1$\alpha$-ol 3.8 g. of active manganese dioxide were added to a solution of 382 mg. of 2$\alpha$-(6-methoxycarbonylhex-cis-2-enyl)-3$\beta$-(3-hydroxyprop-trans-1-enyl)-4$\alpha$-(2-tetrahydropyranyloxy)-cyclopentan-1$\alpha$-ol (prepared as described in Reference Example 6) in 30 ml. of methylene chloride, the mixture stirred at room temperature for 2 hours and filtered. The precipitate was washed thoroughly with acetone, and the filtrate and washings were combined and concentrated under reduced pressure. The residue was purified by column chromatography on silica gel using a mixture of ethyl acetate - benzene (1:4) as eluent to give 266 mg. of the title compound having the following physical characteristics:

IR (liquid film):$\nu$; 3450, 2930, 1737, 1688, 1632, 1435, 1125, 1022, and 977 $cm^{-1}$;
NMR (CDCl$_3$ solution):$\delta$; 9.56 (1H, d), 6.82 and 6.79 (1H, dd, respectively), 6.20 and 6.18 (1H, dd respectively), 5.36 (2H, m), 4.58 (1H, m), 3.61 (3H, s) and 4.30–3.20 (4H, m);
TLC (developing solvent, ethyl acetate - benzene = 1:2); Rf = 0.27.

REFERENCE EXAMPLE 8

1α-Acetoxy-2α-(6-methoxycarbonylhex-cis-2-enyl)-3β-(2-formyl-trans-vinyl)-4α-(2-tetrahydropyranyloxy)-cyclopentane 380 mg. of 2α-(6-methoxycarbonylhex-cis-2-enyl)-3β-(2-formyl-trans-vinyl)-4α-(2-tetrahydropyranyloxy)-cyclopentan-1α-ol (prepared as described in Reference Example 7) were dissolved in 1.61 ml. of pyridine and 1.87 ml. of acetic anhydride were added and stirred at room temperature for 5 hours. The reaction mixture was concentrated under reduced pressure, the residue was dissolved in 50 ml. of ethyl acetate and 5 ml. of 0.05N hydrochloric acid were added. After separation into two layers, the organic layer was washed with an aqueous solution of sodium chloride, dried over magnesium sulphate and concentrated under reduced pressure. The residue was purified by column chromatography on silica gel using a mixture of ethyl acetate - benzene (1:4) as eluent to give 380 mg. of the title compound having the following physical characteristics:

IR (liquid film):$\nu$; 2930, 1737, 1687, 1636, 1244, 1127 and 1030 cm$^{-1}$;

NMR (CDCl$_3$ solution):$\delta$; 9.56 (1H, d), 6.82 and 6.79 (1H, each dd), 6.26 and 6.23 (1H, each dd), 5.34 (2H, m), 5.11 (1H, m), 4.56 (1H, m), 4.27–3.25 (3H, m), 3.67 (3H, s), 2.09 (3H, s) and 3.00–1.26 (18H, m);

TLC (developing solvent, ethyl acetate - benzene = 1:2); Rf = 0.50.

REFERENCE EXAMPLE 9

Methyl 9α-acetoxy-11α-(2-tetrahydropyranyloxy)-15(ξ)-hydroxy-16(ξ)-phenylthio-16-methylthio-17,18,19,20-tetranorprosta-cis-5,trans-13-dienoate 10 ml. of a 1.4M solution of n-butyllithium in n-hexane were added dropwise to a solution of 2.0 ml. of phenylthio-methylthio-methane (prepared as described in Reference Example 1) in 15 ml. of tetrahydrofuran under an atmosphere of nitrogen at −20° C. and the reaction mixture was stirred at the same temperature for 2 hours. 17.8 ml. of the reaction mixture thus obtained were added dropwise at −70° C. to a solution of 2.7 g. of 1α-acetoxy-2α-(6-methoxycarbonylhex-cis-2-enyl)-3β-(2-formyl-trans-vinyl)-4α-(2-tetrahydropyranyloxy)-cyclopentane (prepared as described in Reference Example 8) in 50 ml. of tetrahydrofuran and the reaction mixture was stirred at the same temperature for 1 hour and at 0° C. for a further 30 minutes, poured into dilute aqueous hydrochloric acid and extracted with ethyl acetate. The extracts were washed with water and an aqueous solution of sodium chloride, dried over magnesium sulphate and concentrated under reduced pressure. The residue was purified by column chromatography on silica gel using a mixture of benzene - ethyl acetate as eluent to give 2.84 g. of the title compound having the following physical characteristics:

IR (liquid film):$\nu$; 3450, 1730, 1590, 1430, 1250, 980 cm$^{-1}$;

NMR (CDCl$_3$ solution):$\nu$; 7.65–7.15 (5H, m), 5.85–4.90 (5H, m), 4.90–4.50 (1H, m), 3.65 (3H, s), 2.25 (1.5H, s), 2.21 (1.5H, s), 2.05 (3H, s).

EXAMPLE 1

Methyl 9α-acetoxy-11α,15α-dihydroxy-16(ξ)-phenylthio-16-methylthio-17,18,19,20-tetranorprosta-cis-5,trans-13-dienoate 2.75 g. of methyl 9α-acetoxy-11α-(2-tetrahydropyranyloxy)-15(ξ)-hydroxy-16(ξ)-phenylthio-16-methylthio-17,18,19,20-tetranorprosta-cis-5,trans-13-dienoate (prepared as described in Reference Example 9) were dissolved in a mixture of 40 ml. of tetrahydrofuran and 10 ml. of 1N hydrochloric acid and the reaction mixture was stirred at 40° C. for 2 hours and then extracted with ethyl acetate. The extracts were washed with water and an aqueous solution of sodium chloride, dried over magnesium sulphate and concentrated under reduced pressure. The residue was purified by column chromatography on silica gel using a mixture of benzene - ethyl acetate as eluent to give 810 mg. of the title compound, having the following physical characteristics, 655 mg. of the 15β-hydroxy isomer and 510 mg. of a mixture of them:

TLC (developing solvent, benzene - ethyl acetate = 1:2); Rf = 0.19 (Rf of the 15β-hydroxy isomer = 0.29);

IR (liquid film):$\nu$; 3400, 1730, 1590, 1250, 980 cm$^{-1}$;

NMR (CDCl$_3$ solution):$\delta$; 7.70–7.15 (5H, m), 5.90–4.90 (5H, m), 3.65 (3H, s), 2.25 (1.5H, s), 2.21 (1.5H, s), 2.05 (3H, s).

EXAMPLE 2

9α,11α,15α-Trihydroxy-16(ξ)-phenylthio-16-methylthio-17,18,19,20-tetranorprosta-cis-5,trans-13-dienoic acid [16(ξ)-Phenylthio-16-methylthio-17,18,19,20-tetranor-PGF$_{2\alpha}$]

A solution of 130 mg. of potassium hydroxide in 3 ml. of water was added to a solution of 238 mg. of methyl 9α-acetoxy-11α,15α-dihydroxy-16(ξ)-phenylthio-16-methylthio-17,18,19,20-tetranorprosta-cis-5,trans-13-dienoate (prepared as described in Example 1) in 4 ml. of ethanol, and the reaction mixture was stirred at room temperature for 1.5 hours, then acidified to pH 2 to 3 with an aqueous solution of acetic acid and extracted with ethyl acetate. The extracts were washed with water and an aqueous solution of sodium chloride, dried over magnesium sulphate and concentrated under reduced pressure. The residue was purified by column chromatography on silica gel using a mixture of ethyl acetate - cyclohexane as eluent to give 140 mg. of the title compound having the following physical characteristics:

TLC (developing solvent, chloroform - tetrahydrofuran - acetic acid = 10:2:1); Rf = 0.13;

IR (liquid film):$\nu$; 3360, 1710, 1580, 1250, 980 cm$^{-1}$;

NMR (CDCl$_3$ solution):$\delta$; 7.60–7.20 (5H, m), 5.80–5.55 (2H, m), 5.55–5.25 (2H, m), 4.88 (4H, broad s), 4.40–3.85 (4H, m), 2.24 (1.5H, s), 2.20 (1.5H, s).

REFERENCE EXAMPLE 10

Methyl 9α-acetoxy-11α,15α-bis-(2-tetrahydropyranyloxy)-16(ξ)-phenylthio-16-methylthio-17,18,19,20-tetranorprosta-cis-5,trans-13-dienoate 10 mg. of p-toluenesulphonic acid and 427 mg. of 2,3-dihydropyran were added to a solution of 400 mg. of methyl 9α-acetoxy-11α,15α-dihydroxy-16(ξ)-phenylthio-16-methylthio-17,18,19,20-tetranorprosta-cis-5,trans-13-dienoate (prepared as described in Example 1) in 10 ml. of methylene chloride and the reaction mixture was stirred at room temperature for 20 minutes and then poured into a saturated aqueous solution of sodium bicarbonate and extracted with ethyl acetate. The extracts were washed with water and an aqueous solution of sodium chloride, dried over magnesium sulphate and concentrated under reduced pressure. The residue was purified by column chromatography on silica gel using a mixture of benzene - ethyl acetate as eluent to give 500 mg. of the title compound having the following physical characteristics:

IR (liquid film): ν; 1730, 1580, 1435, 1250, 980 cm$^{-1}$;
NMR (CDCl$_3$ solution): δ; 7.70–7.15 (5H, m), 5.90–4.90 (5H, m), 4.90–4.50 (2H, m), 3.64 (3H, s), 2.25 (3H, s), 2.05 (3H, s).

EXAMPLE 3

Methyl 9α-hydroxy-11α,15α-bis-(2-tetrahydropyranyloxy)-16(ξ)-phenylthio-16-methylthio-17,18,19,20-tetranorprosta-cis-5,trans-13-dienoate A solution of 500 mg. of methyl 9α-acetoxy-11α,15α-bis-(2-tetrahydropyranyloxy)-16(ξ)-phenylthio-16-methylthio-17,18,19,20-tetranorprosta-cis-5,trans-13-dienoate (prepared as described in Reference Example 10) in 7 ml. of methanol was stirred with 122 mg. of anhydrous potassium carbonate at 50° C. for 2 hours. The reaction mixture was poured into dilute aqueous hydrochloric acid and extracted with ethyl acetate. The extracts were washed with water and an aqueous solution of sodium chloride, dried over magnesium sulphate and concentrated under reduced pressure to give 470 mg. of the title compound having the following physical characteristics:

IR (liquid film): ν; 3400, 1730, 1580, 1435, 980 cm$^{-1}$;
NMR (CDCl$_3$ solution): δ; 7.70–7.10 (5H, m), 5.80–5.15 (4H, m), 4.95–4.50 (2H, m), 3.60 (3H, s), 2.24 (3H, s).

EXAMPLE 4

Methyl 9-oxo-11α,15α-bis-(2-tetrahydropyranyloxy)-16(ξ)-phenylthio-16-methylthio-17,18,19,20-tetranorprosta-cis-5,trans-13-dienoate 0.648 ml. of dimethylsulphide was added to a solution of 495 mg. of N-chlorosuccinimide in 15 ml. of toluene at −20° C. After stirring for 1 hour, a solution of 470 mg. of methyl 9α-hydroxy-11α,15α-bis-(2-tetrahydropyranyloxy)-16(ξ)-phenylthio-16-methylthio-17,18,19,20-tetranorprosta-cis-5,trans-13-dienoate (prepared as described in Example 3) in 10 ml. of toluene was added and the reaction mixture was stirred at −20° C. for 2 hours. Then a solution of 0.923 ml. of triethylamine in 1.3 ml. of n-pentane was added to the reaction mixture, which was stirred at room temperature for 10 minutes, diluted with ethyl acetate, washed with aqueous hydrochloric acid, an aqueous solution of sodium bicarbonate and an aqueous solution of sodium chloride, dried over magnesium sulphate and concentrated under reduced pressure. The residue was purified by column chromatography on silica gel using a mixture of benzene and ethyl acetate as eluent to give 329 mg. of the title compound having the following physical characteristics:

IR (liquid film): ν; 1740, 1580, 1440, 980 cm$^{-1}$;
NMR (CDCl$_3$ solution): δ; 7.70–7.15 (5H, m), 5.95–5.20 (4H, m), 4.90–4.50 (2H, m), 3.65(3H, s), 3.00–2.50 (1H, m), 2.26 (3H, s).

EXAMPLE 5

Methyl 9-oxo-11α,15α-dihydroxy-16(ξ)-phenylthio-16-methylthio-17,18,19,20-tetranorprosta-cis-5,trans-13-dienoate

[16(ξ)-Phenylthio-16-methylthio-17,18,19,20-tetranor-PGE$_2$ methyl ester]

327 mg. of methyl 9-oxo-11α,15α-bis-(2-tetrahydropyranyloxy)-16(ξ)-phenylthio-16-methylthio-17,18,19,20-tetranorprosta-cis-5,trans-13-dienoate (prepared as described in Example 4) were dissolved in a mixture of 1 ml. of tetrahydrofuran and 6.7 ml. of a 65% aqueous solution of acetic acid and the reaction mixture was stirred at 40° C. for 2 hours and then extracted with ethyl acetate. The extracts were washed with water and an aqueous solution of sodium chloride, dried over magnesium sulphate and concentrated under reduced pressure. The residue was purified by column chromatography on silica gel using a mixture of ethyl acetate and cyclohexane as eluent to give 153 mg. of the title compound having the following physical characteristics:

TLC (developing solvent, chloroform - tetrahydrofuran - acetic acid = 10:2:1); Rf = 0.53;
IR (liquid film): ν; 3400, 1735, 1580, 1435, 980 cm$^{-1}$;
NMR (CDCl$_3$ solution): δ; 7.60–7.25 (5H, m), 5.90–5.70 (2H, m), 5.53–5.25 (2H, m), 4.45–3.95 (3H, m), 3.65 (3H, s), 3.80–3.30 (2H, m), 2.90–2.58 (1H, m), 2.27 (1.5H, s), 2.24 (1.5H, s).

REFERENCE EXAMPLE 11

1α-Acetoxy-2α-(6-methoxycarbonylhexyl)-3β-formyl-4α-(2-tetrahydropyranyloxy)-cyclopentane 700 mg. of 5% palladium on carbon were suspended in 30 ml. of methanol, the air in the apparatus was replaced by hydrogen, and a solution of 2.0 g. of 1α-acetoxy-2α-(6-methoxycarbonylhex-cis-2-enyl)-3β-formyl-4α-(2-tetrahydropyranyloxy)-cyclopentane (prepared as described hereinafter) in 10 ml. of methanol was added thereto. Catalytic reduction of the compound was carried out at room temperature under ambient pressure for 10 minutes. After completion of the reaction, the catalyst was filtered off and the filtrate was concentrated under reduced pressure to give 1.95 g. of the title compound having the following physical characteristics:

IR (liquid film): ν; 2930, 1740, 1440, 1250, 1030 cm$^{-1}$;
NMR (CDCl$_3$ solution): δ; 9.66 (1H, t), 5.25–4.90 (1H, m), 3.65 (3H, s), 2.06 (3H, s).

1α-Acetoxy-2α-(6-methoxycarbonylhex-cis-2-enyl)-3β-formyl-4α-(2-tetrahydropyranyloxy)-cyclopentane, used as a starting material in the above procedure, may be prepared from 2-oxa-3-oxo-6-syn-hydroxymethyl-7-antiacetoxy-cis-bicyclo[3,3,0]octane, [prepared as described by E. J. Corey et al., J. Am. Chem. Soc., 92, 397, (1970)], as follows:

190 g. of 2-oxa-3-oxo-6-syn-hydroxymethyl-7-antiacetoxy-cis-bicyclo[3,3,0]octane in 1.5 liters of absolute methanol and 130 g. of potassium carbonate were stirred at room temperature for 1 hour, and then successively cooled in an ice-bath, and neutralized with hydrochloric acid. The precipitate was filtered off and the filtrate was concentrated under reduced pressure. The residue was washed with ethanol, and then with ethyl acetate, and dried to give 124 g. of 2-oxa-3-oxo-6-syn-hydroxymethyl-7-anti-hydroxy-cis-bicyclo[3,3,0]octane as white crystallites having the following physical characteristics:

m.p. : 119° C.;

IR (KBr tablet): $\nu$; 3350, 2970–2880, 1740, 1480, 1440, 1410, 1380, 1335, 1305, 1270, 1205, 1100, 1080, 1060, 1040, 1020, 1000 and 975 cm$^{-1}$;

NMR (in CDCl$_3$ + deutero dimethyl sulphoxide solution): $\delta$; 5.10–4.60 (1H, m), 4.29 (2H, s), 4.13–3.77 (1H, m) and 3.38 (2H, d);

TLC (developing solvent, methylene chloride - methanol = 20:1); Rf = 0.27.

124 g. of 2-oxa-3-oxo-6-syn-hydroxymethyl-7-anti-hydroxy-cis-bicyclo[3,3,0]octane, obtained as described above, were dissolved in absolute pyridine (1.4 liters) and cooled to −40° C. 74 g. of acetic anhydride were added dropwise and the mixture stirred for 5 hours at −40 to −20° C. and then for 16 hours at 0° C. The pyridine was evaporated off under reduced pressure and the residue was dissolved in 1 liter of ethyl acetate. 200 g. of sodium bisulphate were added, and the solution was stirred vigorously and filtered. The filtrate was concentrated under reduced pressure and the residue was purified by column chromatography on silica gel using a mixture of benzene and ethyl acetate (1:3) as eluent to give 112 g. of 2-oxa-3-oxo-6-syn-acetoxymethyl-7-anti-hydroxy-cis-bicyclo[3,3,0]octane as colourless needles having the following physical characteristics:

m.p. : 36–37° C.;

IR (KBr tablet): $\nu$; 3450, 2960, 2850, 1775, 1740, 1420, 1370, 1250, 1190, 1120, 1090, 1040 and 980 cm$^{-1}$;

NMR (CDCl$_3$ solution): $\delta$; 5.15–4.60 (1H, m), 4.3–3.75 (3H, m), 3.50 (1H, s) and 2.02 (3H, s);

TLC (developing solvent, methylene chloride - methanol = 20:1); Rf =0.50.

4.3 g. of 2-oxa-3-oxo-6-syn-acetoxymethyl-7-anti-hydroxy-cis-bicyclo[3,3,0]octane, obtained as described above, were dissolved in 520 ml. of methylene chloride, 25 g. of dihydropyran and 0.52 g. of p-toluenesulphonic acid were added and the mixture stirred for 20 minutes at room temperature. The reaction mixture was neutralized with an aqueous solution of sodium bicarbonate, diluted with ethyl acetate, washed with water, dried and concentrated under reduced pressure to give 56 g. of 2-oxa-3-oxo-6-syn-acetoxymethyl-7-anti-(2-tetrahydropyranyloxy)-cis-bicyclo[3,3,0]octane as a colourless oil having the following physical characteristics:

IR (liquid film): $\nu$; 2950–2840, 1775, 1740, 1465, 1440, 1390–1340, 1240, 1180, 1140–1120, 1080, 1040 and 980 cm$^{-1}$;

NMR (CDCl$_3$ solution): $\delta$; 5.2–4.72 (1H, m), 4.72–4.30 (1H, m), 4.2–3.2 (5H, m) and 2.01 (3H, s);

TLC (developing solvent, methylene chloride-methanol = 20:1); Rf = 0.74.

56 g. of the acetyl ether, prepared as described above, were dissolved in 900 ml. of toluene and cooled to −60° C. 456 ml. of a 25(w/v)% solution of diisobutylaluminium hydride in toluene were added, and the solution was stirred for 20 minutes at the same temperature; methanol was added in order to decompose the excess of diisobutylaluminium hydride and water was added. The resulting precipitate was filtered off and the filtrate was dried and concentrated under reduced pressure to give 35.2 g. of 2-oxa-3-hydroxy-6-syn-hydroxymethyl-7-anti-(2-tetrahydropyranyloxy)-cis-bicyclo[3,3,0]octane as a colourless oil having the following physical characteristics:

IR (liquid film); $\nu$; 3400, 2940–2860, 1465–1440, 1380, 1355, 1325, 1260, 1200, 1140, 1120, 1075 and 1020 cm$^{-1}$;

TLC (developing solvent, ethyl acetate); Rf = 0.25.

37.6 g. of sodium hydride (content 63.5%) were suspended in 400 ml. of dimethyl sulphoxide and stirred at 70° C. for 1.5 hours to obtain sodium methylsulphinylmethylide. The reaction mixture was allowed to cool to room temperature and then added dropwise to a solution of 226 g. of (4-carboxybutyl)triphenylphosphonium bromide in 460 ml. of dimethyl sulphoxide, the reaction temperature being kept within the range 20 to 25° C.

A solution of 35.2 g. of 2-oxa-3-hydroxy-6-syn-hydroxymethyl-7-anti-(2-tetrahydropyranyloxy)-cis-bicyclo[3,3,0]octane, prepared as described above, in 90 ml. of dimethyl sulphoxide was added to the above reaction mixture and stirred at 35 to 40° C. for 1.5 hours. The reaction mixture was poured into 6 liters of ice-water and the neutral substances were removed by extraction with an ethyl acetate-diethyl ether mixture (1:1). The aqueous layer was acidified to pH 2 with a saturated aqueous solution of oxalic acid and extracted with a diethyl ether-n-pentane mixture (1:1). The organic layer was washed with water, dried over sodium sulphate and concentrated under reduced pressure. The residue was subjected to column chromatography on silica gel using a mixture of benzene and methanol (10:1) as eluent to give 35 g. of 2α-(6-carboxyhex-cis-2-enyl)-3β-hydroxymethyl-4α-(2-tetrahydropyranyloxy)-cyclopentan-1α-ol as a colourless oil having the following physical characteristics:

(liquid film): $\nu$; 3400, 2940–2860, -2300, 1710, 1450, 1435, 1400, 1355, 1245, 1200, 1140, 1120, 1075 and 1025 cm$^{-1}$;

NMR (in CDCl$_3$ solution): $\delta$; 6.20 (3H, s), 5.50–5.10 (2H, m), 4.75–4.36 (1H, m), 4.24–3.85 (2H, m) and 3.85–3.0 (4H, m);

TLC (developing solvent, chloroform - tetrahydrofuran - acetic acid = 10:2:1); Rf = 0.53.

To a solution of 18.8 g. of 2α-(6-carboxyhex-cis-2-enyl)-3β-hydroxymethyl-4α-(2-tetrahydropyranyloxy)-cyclopentan-1α-ol, obtained as described above, in 130 ml. of diethyl ether, a freshly prepared ethereal solution of diazomethane was added with cooling in an ice-bath until the reaction mixture showed a pale yellow colour. The reaction mixture was concentrated in vacuo, and the residue was subjected to column chromatography on silica gel using a mixture of cyclohexane and ethyl acetate (2:1) as eluent to give 15.4 g. of 2α-(6-methoxycarbonyl-hex-cis-2-enyl)-3β-hydroxymethyl-4α-(2-tetrahydropyranyloxy)-cyclopentan-1α-ol as a colourless oil having the following physical characteristics:

IR (liquid film): $\nu$; 3450, 2950, -2870, 1740, 1440, 1360, 1325, 1250, 1200, 1140, 1120, 1080 and 1025 cm$^{-1}$;

NMR (in CDCl$_3$ solution): $\delta$; 5.55–5.00 (2H, m), 4.78–4.30 (1H, m), 4.20–3.06 (6H, m), 3.55 (3H, s) and 2.97 (2H, s);

TLC (developing solvent, methylene chloride - methanol = 19:1); Rf = 0.43.

13.1 g. of 2α-(6-methoxycarbonylhex-cis-2-enyl)-3β-hydroxymethyl-4α-(2-tetrahydropyranyloxy)-cyclopentan-1α-ol, obtained as described above, were dissolved in 250 ml. of absolute methylene chloride, and 25 ml. of pyridine were added. The air in the apparatus was replaced with nitrogen and the contents cooled to −20° C. To the reaction mixture was added dropwise a solution of 5.1 ml. of trimethylchlorosilane in 30 ml. of methylene chloride with stirring and the mixture was then stirred at the same temperature for 30 minutes. A sample of the product thus obtained had the following physical characteristic:
TLC (developing solvent, benzene - ethyl acetate = 2:1); Rf = 0.61.

A solution of 2.9 ml. of acetyl chloride in 20 ml. of methylene chloride was added dropwise to the above reaction mixture and stirred at room temperature for 30 minutes. Then 2 ml. of ethanol were added to decompose the excess of acetyl chloride. Pyridine in the reaction mixture was neutralized by the addition of 50 g. of sodium bisulphate, and the resulting precipitate was filtered off. The filtrate was concentrated under reduced pressure to give a residue having the following physical characteristic:
TLC (developing solvent, benzene - ethyl acetate = 2:1); Rf = 0.82.

The residue was dissolved in 300 ml. of ethyl acetate, 100 ml. of an aqueous solution of oxalic acid were added and the solution was stirred vigorously at room temperature. The organic layer was separated, washed successively with water, an aqueous solution of sodium bisulphate, water and an aqueous solution of sodium chloride, dried with sodium sulphate and concentrated under reduced pressure to give 13.7 g. of crude product. The crude product was subjected to column chromatography on silica gel using a mixture of benzene and ethyl acetate (3:1) as eluent to give 7.45 g. of 1α-acetoxy-2α-(6-methoxycarbonylhex-cis-2-enyl)-3β-hydroxymethyl-4α-(2-tetrahydropyranyloxy)-cyclopentane, 2.40 g. of 1α-hydroxy-2α-(6-methoxycarbonyl-hex-cis-2-enyl)-3β-hydroxymethyl-4α-(2-tetrahydropyranyloxy)-cyclopentane, 720 mg. of 1α-hydroxy-2α-(6-methoxycarbonylhex-cis-2-enyl)-3β-acetoxymethyl-4α-(2-tetrahydropyranyloxy)-cyclopentane, and 1.45 g. of 1α-acetoxy-2α-(6-methoxycarbonylhex-cis-2-enyl)-3β-acetoxymethyl-4α-(2-tetrahydropyranyloxy)-cyclopentane.

1α-Acetoxy-2α-(6-methoxycarbonylhex-cis-2-enyl)-3β-hydroxymethyl-4α-(2-tetrahydropyranyloxy)-cyclopentane had the following physical characteristics:
IR (liquid film): ν; 3450, 3000, 2950, 2870, 1740, 1440, 1380, 1330, 1250, 1200, 1160, 1140, 1080, 1030, 980, 920, 875 and 815 cm$^{-1}$;
NMR (in CDCl$_3$ solution): δ; 5.45–5.27 (2H, m), 5.16–4.92 (1H, m), 4.76–4.46 (1H, m), 4.27–3.96 (1H, m), 3.67 (3H, s), 2.98–2.64 (1H, m) and 2.05 (3H, s);
TLC (developing solvent, benzene - ethyl acetate = 2:1); Rf = 0.27.

Under an atmosphere of nitrogen, 4.4 ml. of pyridine were dissolved in 80 ml. of methylene chloride, 2.88 g. of chromium trioxide were added with stirring and the solution was stirred for 15 minutes. 12 g. of infusorial earth were added to the reaction mixture, and then there was added a solution of 956 mg. of 1α-acetoxy-2α-(6-methoxycarbonylhex-cis-2-enyl)-3β-hydroxymethyl-4α-(2-tetrahydropyranyloxy)-cyclopentane, prepared as described above, in 20 ml. of methylene chloride. After stirring for 10 minutes, 20 g. of sodium bisulphate were added to the reaction mixture and stirring continued for a further 10 minutes. The resulting precipitate was filtered off and the filtrate was concentrated under reduced pressure. The residue was subjected to column chromatography on silica gel using a mixture of benzene and ethyl acetate (5:1) as eluent to give 1α-acetoxy-2α-(6-methoxycarbonylhex-cis-2-enyl)-3β-formyl-4α-(2-tetrahydropranyloxy)cyclopentane as a colourless oil having the following physical charcteristics:
IR (liquid film): ν; 3000, 2950, 2860, 2725, 1740, 1440, 1380, 1325, 1255, 1200, 1165, 1140, 1085, 1030, 980, 920, 880 and 820 cm$^{-1}$;
NMR (in CDCl$_3$ solution): δ; 9.85–9.68 (1H, m), 5.45–4.96 (1H, m), 4.68–4.48 (1H, m), 4.48–4.25 (1H, m), 3.67 (3H, s) and 2.08 (3H, s);
TLC (developing solvent, benzene - ethyl acetate = 2:1); RF = 0.66.

REFERENCE EXAMPLE 12

1α-Acetoxy-2α-(6-methoxycarbonylhexyl)-3β-(2-formyl-trans-vinyl)-4α-(2-tetrahydropyranyloxy)-cyclopentane 1.95 g. of 1α-acetoxy-2α-(6-methoxycarbonylhexyl)-3β-formyl-4α-(2-tetrahydropyranyloxy)-cyclopentane (prepared as described in Reference Example 11) and 1.57 g. of formylmethylenetriphenylphosphorane (prepared as described in J. Chem. Soc., 1961, 1268) were dissolved in 25 ml. of dry benzene and the solution was stirred at 70° C. for 20 hours. The reaction mixture was then purified by column chromatography on silica gel using a mixture of benzene and ethyl acetate as eluent to give 1.73 g. of the title compound having the following physical characteristics:
IR (liquid film): ν; 1740, 1690, 1640, 1440, 1250, 1030 cm$^{-1}$;
NMR (CDCl$_3$ solution): δ; 7.00–5.90 (2H, m), 5.30–4.90 (1H, m), 4.70–4.40 (1H, m), 3.65 (3H, s), 2.06 (3H, s).

REFERENCE EXAMPLE 13

Methyl 9α-acetoxy-11α-(2-tetrahydropyranyloxy)-15(ξ)-hydroxy-16(ξ)-phenylthio-16-methylthio-17,18,19,20-tetranorprost-trans-13-enoate By proceeding as described in Reference Example 9 but utilising 13.2 ml. of the reaction mixture obtained from 7.5 ml. of a 1.4M solution of n-butyl- lithium in n-hexane and a solution of 1.5 ml. of phenylthio-methylthio-methane in 11 ml. of tetrahydrofuran and replacing the 1α-acetoxy-2α-(6-methoxycarbonylhex-cis-2-enyl)-3β-(2-formyl-trans-vinyl)-4α-(2-tetrahydropyranyloxy)cyclopentane by 1.7 g. of 1α-acetoxy-2α-(6-methoxycarbonylhexyl)-3β-(2-formyl-trans-vinyl)-4α-(2-tetrahydropyranyloxy)-cyclopentane (prepared as described in Reference Example 12) in 35ml. of tetrahydrofuran there were obtained 2.0 g. of the title compound having the following physical characteristics:
IR (liquid film): ν; 3450, 1740, 1590, 1430, 1250, 980 cm$^{-1}$;
NMR (CDCl$_3$ solution): δ; 7.65–7.15 (5H, m), 5.80–5.50 (2H, m), 5.20–4.90 (1H, m), 4.90–4.50 (1H, m), 3.65 (3H, s), 2.25 (1.5H, s), 2.21 (1.5H, s), 2.05 (3H, s).

EXAMPLE 6

Methyl 9α-acetoxy-11α,15α-dihydroxy-16(ξ)-phenylthio-16-methylthio-17,18,19,20-tetranorprost-trans-13-enoate By proceeding as described in Example 1 but replacing the methyl 9α-acetoxy-11α-(2 -tetrahydropyranyloxy)-15(ξ)-hydroxy-16(ξ)-phenylthio-16-methylthio-17,18,19,20-tetranorprosta-cis-5,trans-13-dienoate by 2.0 g. of methyl 9α-acetoxy-11α-(2-tetrahydropyranyloxy)-15(ξ)-hydroxy-16(ξ)-phenylthio-16- methylthio-17,18,19,20-tetranorprost-trans-13-enoate (prepared as described in Reference Example 13) and utilising a mixture of 30 ml. of tetrahydrofuran and 7 ml. of 1N hydrochloric acid there were obtained 475 mg. of the title compound, having the following physical characteristics, 490 mg. of the 15β-hydroxy isomer and 230 mg. of a mixture of them:

TLC (developing solvent, benzene - ethyl acetate = 1:2); Rf = 0.20, (Rf of the 15β-hydroxy isomer = 0.30);

IR (liquid film): ν; 3400, 1740, 1710, 1590, 1250, 980 $cm^{-1}$;

NMR (CDCl$_3$ solution): δ; 7.60–7.05 (5H, m), 5.75–5.45 (2H, m), 5.30–4.90 (1H, m), 3.62 (3H, s), 2.25 (1.5H, s), 2.21 (1.5H, s), 2.05 (3H, s).

REFERENCE EXAMPLE 14

Methyl 9α-acetoxy-11α,15α-bis-(2-tetrahydropranyloxy)-16(ξ)-phenylthio-16-methylthio-17,18,19,20-tetranorprost-trans-13-enoate By proceeding as described in Reference Example 10 but replacing the methyl 9α-acetoxy-11α,15α-dihydroxy-16(ξ)-phenylthio-16-methylthio-17,18,19,20-tetranorprosta-cis-5,trans-13-dienoate by 375 mg. of methyl 9α-acetoxy-11α,15α-dihydroxy-16(ξ)-phenylthio-16-methylthio-17,18,19,20-tetranorprost-trans-13-enoate (prepared as described in Example 6) dissolved in 8 ml. of methylene chloride, and utilising 7 mg. of p-toluenesulphonic acid and 0.34 ml. of 2,3-dihydropyran there were obtained 420 mg. of the title compound having the following physical characteristics:

IR (liquid film): ν; 1740, 1590, 1440, 1250, 1030 $cm^{-1}$;
NMR (CDCl$_3$ solution): δ; 7.60–7.00 (5H, m), 5.80–5.40 (2H, m), 5.20–4.90 (1H, m), 4.90–4.50 (2H, m), 3.61 (3H, s), 2.23 (3H, s), 2.02 (3H, s).

EXAMPLE 7

Methyl 9α-hydroxy-11α,15α-bis-(2-tetrahydrpyranyloxy)-18 16(ξ)-phenylthio-16-methylthio-17,18,19,20-tetranorprost-trans-13-enoate By proceeding as described in Example 3 but replacing the methyl 9α-acetoxy-11α15α-bis-(2-tetrahydropranyloxy)-16(ξ)-phenylthio-16-methylthio-17,18,19,20-tetranorprosta-cis-5,trans-13-dienoate by 420 mg. of methyl 9α-acetoxy-11α,15α-bis-(2-tetrhydropranyloxy)-16(ξ)-phenylthio-16-methylthio-17,18,19,20-tetranorprost-trans-13-enoate (prepared as described in Reference Example 14) dissolved in 6 ml. of methanol and utilising 103 mg. of anhydrous potassium carbonate there were obtained 395 mg. of the title compound having the following physical characteristics:

IR (liquid film): ν; 3450, 1740, 1440, 1030, 980 $cm^{-1}$;
NMR (CDCl$_3$ solution): δ; 7.60–7.00 (5H, m), 5.80–5.45 (2H, m), 4.90–4.50 (2H, m), 3.62 (3H, s), 2.23 (3H, s).

EXAMPLE 8

Methyl 9-oxo-11α,15α-bis-(2-tetrahydropyranyloxy)-16(ξ)-phenylthio-16-methylthio-17,18,19,20-tetranoroprost-trans-13-enoate By proceeding as described in Example 4 but utilising 0.543 ml. of dimethylsulphide and a solution of 414 mg. of N-chlorosuccinimide in 13 ml. of toluene, replacing the methyl 9α-hydroxy-11α,15α-bis-(2-tetrahydropyranyloxy)-16(ξ)-phenylthio-16-methylthio-17,18,19,20-tetranorprosta-cis-[5,trans-13-dienoate by 395 mg. of methyl 9α-hydroxy-11α,15α-bis-(2-tetrahydropyranyloxy)- 16(ξ)-phenylthio-16-methylthio-17,18,19,20-tetranorprost-trans-13-enoate (prepared as described in Example 7) dissolved in 9 ml. of toluene and utilising a solution of 0.78 ml. of triethylamine in 1.1 ml. of n-pentane there were obtained 235 mg. of the title compound having the following physical characteristics:

IR (liquid film):ν; 1740, 1710, 1590, 1440, 1030 $cm^{-1}$;
NMR (CDCl$_3$ solution):δ; 7.60–7.10 (5H, m), 5.95–5.55 (2H, m), 4.85–4.50 (2H, m), 3.62 (3H, s) 2.25 (3H, s).

EXAMPLE 9

Methyl 9-oxo-11αα,15α-dihydroxy-16(ξ)-phenylthio-16-methylthio-17,18,19,20-tetranorprost-trans-13-enoate
[16(ξ)-Phenylthio-16-methylthio-17,18,19,20-tetranor-PGE$_1$ methyl ester]

By proceeding as described in Example 5 but replacing the methyl 9-oxo-11α,15α-bis-(2-tetrahydropyranyloxy)-16(ξ)-phenylthio-16-methylthio-17,18,19,20-tetranorprosta-cis-5,trans-13-dienoate by 285 mg. of methyl 9-oxo-11α,15α-bis-(2-tetrahydropyranyloxy)-16(ξ)-phenylthio- 16-methylthio-17,18,18,20-tetranorprost-trans-13-enoate (prepared as described in Example 8) and utilising a mixture of 0.9 ml. of tetrahydrofuran and 5.8 ml. of a 65% aqueous solution of acetic acid there were obtained 150 mg. of the title compound having the following physical characteristics:

IR (liquid film):ν; 3400, 1740, 1590, 1440, 980 $cm^{-1}$;
NMR (CDCl$_3$ solution):δ; 7.60–7.25 (5H, m), 5.90–5.70 (2H, m), 4.20–3.95 (2H, m), 3.65 (3H, s), 3.50–3.20 (2H, m), 2.90–2.58 (1H, m), 2.27 (1.5H, s), 2.24 (1.5H, s);
TLC (developing solvent, ethyl acetate); Rf = 0.50.

REFERENCE EXAMPLE 15

Methyl 9α-acetoxy-11α-(2-tetrahydropyranyloxy)-15α-hydroxy-15-[2-(1,3-dithiacyclohexyl)]-16,17,18,19,20-pentanorprosta-cis-5,trans-13-dienoate 13.2 ml. of a 0.5M solution of n-butyllithium in n-hexane were added dropwise to a solution of 720 mg. of 1,3-dithiane in 25 ml. of anhydrous tetrahydrofuran under an atmosphere of nitrogen at −25° C. and the reaction mixture was stirred for 2 hours to give lithio-1,3-dithiane. 2.028 g. of 1α-acetoxy-2α-(6-methoxycarbonylhex-cis-2-enyl)-3β-(2-formyl-trans-vinyl)-4α-(2-tetrahydropyranyloxy)-cyclopentane (prepared as described in Reference Example 8) were dissolved in 20 ml. of tetrahydrofuran, cooled to a temperature below -60° C. and, under an atmosphere of nitrogen, the lithio-1,3-dithiane solution, obtained above, was added slowly. the reaction mixture was stirred for 40 minutes and then acidified with 2ml. of acetic acid. After evaporation of the solvent under reduced pressure, the residue was dissolved in ethyl acetate, washed with water, an aqueous solution of sodium bicarbonate and an aqueous solution of sodium chloride, dried over sodium sulphate and concentrated under reduced pressure. The residue was separated and purified by column chromatography on silica gel using a mixture of benzene and ethyl acetate (4:1) as eluent to give 852 mg. of the title compound, having the following physical characteristics, 604 mg. of the 15β-hydroxy isomer and 594 mg. of the starting formyl compound:

IR (liguid film):ν; 3440, 2940, 2900, 2865, 1730, 1435, 1380, 1360, 1330, 1250, 1175, 1140, 1085, 1030, 975, 920, 875 cm$^{-1}$;

NMR (CDCl$_3$ solution):δ; 5.90–5.60 (2H, m), 5.55–5.20 (2H, m), 5.20–4.85 (1H, m), 4.85–4.50 (1H, m), 4.50–3.15 (8H, m), 3.15–2.65 (4H, m), 2.05 (3H, s);

TLC (developing solvent, benzene - ethyl acetate = 1:1);

Rf = 0.53, (Rf of 15β-hydroxy isomer = 0.59).

REFERENCE EXAMPLE 16

Methyl 9α-acetoxy-11α,15α-bis-(2-tetrahydropyranyloxy)-15-[2-(1,3-dithiacyclohexyl)]-16,17,18,19,20-pentanorprosta-cis-5,trans-13-dienoate 1.48 g. of methyl 9α-acetoxy11α-(2-tetrahydropyranyloxy)-15α-hydroxy-15-[2-(1,3-dithiacyclohexy)]-16,17,18,19,20-pentanorprosta-cis-5,trans-13-dienoate (prepared as described in Reference Example 15) were dissolved in 15 ml. of methylene chloride and the solution was reacted with 0.5 ml. of 2,3-dihydropyran and 8 mg. of p-toluenesulphonic acid at room temperature for 15 minutes. The reaction mixture was diluted with ethyl acetate, washed with an aqueous solution of sodium bicarbonate and an aqueous solution of sodium chloride, dried over sodium sulphate and concentrated under reduced pressure to give 1.7 g. of the title compound having the following physical characteristics:

IR (liquid film;ν; 2940, 2860, 1740, 1455, 1440, 1385, 1355, 1315, 1250, 1200, 1185, 1160, 1130, 1080, 1040, 1030, 975, 920, 875 cm$^{-1}$;

NMR (CDCl$_3$ solution):δ; 5.00–5.20 (4H, m), 5.20–4.80 (1H, m), 4.80–4.45 (2H, m), 4.45–3.15 (10H, m), 3.15–2.65 (4H, m), 2.05 (3H, s);

TLC (developing solvent, benzene - ethyl acetate = 2:1);

Rf = 0.62.

EXAMPLE 10

9α-Hydroxy-11α,15α-bis(2-tetrahydropyranyloxy)-15-[2-(1,3-dithiacyclohexyl)]-16,17,18,19,20-pentanorporosta-cis-5,trans-13-dienoic acid 660 mg. of methyl 9α-acetoxy-11α,15α-bis-(2-tetrahydropyranyloxy)-15-[2-(1,3-dithiacyclohexyl)]-16,17,18,19,20-pentanorprosta-cis-5,trans-13-dienoate (prepared as described in Reference Example 16) were dissolved in a mixture of 2 ml. of 4N potassium hydroxide and 7 ml. of methanol and the solution stirred at toom temperture for 1 hour. The reaction mixture was acidified with an aqueous solution of oxalic acid and extracted with ehtyl acetate. The organic extracts were washed with water and an aqueous solution of sodium chloride, dried over sodium sulphate and concentrated under reduced pressure to give 580 mg. of the title compound having the following physical characteristics:

IR (liquid film):ν; 3660, 2950, 2860, 1740, 1710, 1455, 1440, 1380, 1360, 1325, 1285, 1270, 1250, 1195, 1180, 1135, 1080, 1040, 1025, 980, 920, 875 cm$^{-1}$;

NMR (CDCl$_3$ solution):δ; 8.40 (2H, s), 5.95–5.20 (4H, m), 5.15–4.55 (2H, m), 4.45–3.20 (8H, m), 3.20–2.65 (4H, m);

TLC (developing solvent, methylene chloride - methanol = 19:1);

Rf = 0.23.

EXAMPLE 11

15-[2-(1,3-Dithiacyclohexyl)]-16,17,18,19,20-pentanorprostaglandin-F$_{2α}$ 580 mg. of 9α-hydroxy-11α,15α-bis-(2-tetrahydropyranyloxy)-15-[2-(1,3-dithiacyclohexyl)]-16,17,18,19,20-pentanorprosta-cis-5,trans-13-dienoic acid (prepared as described in Example 10) were dissolved in 5.5 ml. of a mixture of acetic acid, water and tetrahydrofuran (65:35:10) and the solution stirred at 40 to 45° C. for 1.5 hours. The reaction mixture was diluted with 50 ml. of ethyl acetate, washed with water and an aqueous solution of sodium chloride, dried over sodium sulphate and concentrated under reduced pressure. The residue was purified by column chromatography on silica gel using a mixture of ethyl acetate and n-hexane (2:1) as eluent to give 220 mg. of the title compound having the following physical characteristics:

IR (liquid film):ν; 3680, 3000, 2930, 1730, 1710, 1420, 1380, 1285, 1250, 1175, 1120, 1050, 975, 915, 870 cm$^{-1}$;

NMR (CDCl$_3$ + DMSO-d$_6$ solution):δ; 5.73–4.16 (4H, m), 4.78 (4H, broad s), 4.39–3.70 (4H, m), 3.10–2.55 (4H, m);

TLC (developing solvent, chloroform - tetrahydrofuran - acetate acid = 10:2:1);

Rf = 0.11;

Optical Rotation: $[α]_D^{23}$ = +44.4° (c=1.0, CHCl$_3$).

EXAMPLE 12

Methyl 9α-hydroxy-11α,15α-bis-(2-tetrahydropyranyloxy)-15-[2-(1,3-dithiacyclohexyl)]-16,17,18,19,20-pentanorprosta-cis-5,trans-13-dienoate 1.04 g. of methyl 9α-acetoxy-11α,15α,-bis-(2-tetrahydropyranyloxy)-15-[2-(1,3-dithiacyclohexyl)]-16,17,18,19,20-pentanorprosta-cis-5,trans-13-dienoate (prepared as described in Reference Example 16) were dissolved in 15 ml. of absolute methanol and the solution stirred with 300 mg. of potassium carbonate at 40 to 45° C. for 2 hours. The reaction mixture ws then poured into a chilled mixture of dilute hydrochloric acid and ethyl acetate and extracted with ethyl acetate. The organic extracts were washed with an aqeuous solution of sodium bicarbonate and an aqueous solution of sodium chloride, dried over sodium sulphate and concentrated under reduced pessure to give 782 mg. of the title compound having the following physical characteristics:

IR (liquid film):ν; 3460, 2945, 1740, 1455, 1440, 1380, 1360, 1325, 1285, 1250, 1200, 1185, 1160, 1130, 1080, 1040, 1020, 980, 920, 875 cm$^{-1}$;

NMR (CDCl$_3$ solution):δ; 5.80–5.05 (4H, m), 5.05–4.45 (2H, m), 4.45–3.10 (11H, m), 3.10–2.60 (4H, m);

TLC (developing solvent, benzene - ethyl acetate = 2:1);

Rf = 0.39.

EXAMPLE 13

Methyl 9-oxo-11α,15α-bis-(2-tetrahydropyranyloxy)-15-[2-(1,3-dithiacyclohexyl)]-16,17,18,19,20-pentanorprosta-cis-5,trans-13-dienoate Under an atmosphere of nitrogen, 2 ml. of dimethyl sulphide were added to a solution of N-chlorosuccinimide in 20 ml. of toluene and the solution stirred for 10 minutes at 0° C. and then for 1 hour at −24° C. A solution of 595 mg. of methyl 9α-hydroxy-11α,15α-bis-(2-tetrahydropyranyloxy)-15-[2-(1,3-dithiacyclohexyl)]-16,17,18,19,20-pentanorprosta-cis-5,trans-13-dienoate (prepared as described in Example 12) in 20 ml. of toluene was added dropwise to the reaction mixture at −50° C. and stirred for 2 hours at −25° C. A solution of 2 ml. of triethylamine in 2 ml. of n-pentane was added to the mixture, which was then diluted with diethyl ether and stirred for 10 minutes. The reaction mixture was diluted with ethyl acetate, washed successively with chilled hydrochloric acid, water, an aqueous solution of sodium bicarbonate and an aqueous solution of sodium chloride, dried over sodium sulphate and concentrated under reduced pressure. The residue was purified by column chromatography on silica gel using a mixture of benzene and ehtyl acetate (7:1) as eluent to give 547 mg. of the title compound having the following physical characteristics:

IR (liquid film):ν; 2940, 1745, 1455, 1440, 1380, 1360, 1330, 1250, 1200, 1160, 1130, 1080, 1040, 1025, 980, 920, 875 cm$^{-1}$;

NMR (CDCl$_3$ solution):δ; 5.85–5.20 (4H, m), 4.90–4.50 (2H, m), 4.35–3.25 (10H, m), 3.05–2.47 (5H, m);

TLC (developing solvent, benzene - ethyl acetate = 2:1);

Rf = 0.61.

EXAMPLE 14

15-[2-(1,3-dithiacyclohexyl)]-16,17,18,19,20-pentanor-PGE$_2$ methyl ester 547 mg. of methyl 9-oxo-11α,15α-bis-(2-tetrahydropyranyloxy)-15-[2-(1,3,-dithiacyclohexyl)]-16,17,18,19,20-pentanorprosta-cis-5,trans-13-dienoate (prepared as described in Example 13) were dissolved in 5.5 ml. of a mixture of acetic acid, water and tetrahydrofuran (65:35:10) and the solution stirred at 40° to 45° C. for 1.5 hours. The reaction mixture was then diluted with 50 ml. of ethyl acetate, washed with water and an aqueous solution of sodium chloride, dried over sodium sulphate and concentrated under reduced pressure. The residue was purified by column chromatography on silica gel using a mixture of ethyl acetate and n-hexane (1:1) as eluent to give 234 mg. of the title compound having the following physical characteristics:

IR (liquid film):ν; 3400, 3000, 2950, 2900, 1740, 1440, 1370, 1320, 1285, 1255, 1160, 1085, 1035, 975, 915, 880 cm$^{-1}$;

NMR (CDCl$_3$ solution):δ; 5.83–5.65 (2H, m), 5.50–5.26 (2H, m), 4.48–4.28 (1H, m), 4.28–3.38 (2H, m), 3.66 (3H, s), 3.23 (3H, s), 3.00–2.55 (5H, m);

TLC (developing solvent, chloroform - tetrahydrofuran - acetic acid = 10:2:1);

Rf = 0.40.

REFERENCE EXAMPLE 17

2-n-Butyl-1,3-dithiane 30 ml. of a 1.6M solution of n-butyllithium in n-hexane were added dropwise to a solution of 4.8 g. of 1,3-dithiane in 150 ml. of tetrahydrofuran under an atmosphere of nitrogen at −20° to −25° C. After 2 hours stirring, 6 g. of n-butyl bromide in 60 ml. of tetrahydrofuran were added dropwise to the reaction mixture, which was stirred for 1 hour at −20° to −25° C. and for a further 30 minutes at room temperture and then concentrated under reduced pressure. The residue was dissolved in diethyl ether, washed with water and an aqueous solution of sodium chloride, dried over magnesium sulphate and concentrated under reduced pressure to give 6.8 g. of the title compound having the following physical characteristics:

IR (CHCl$_3$ solution):ν: 2960, 2940, 2860, 1465, 1430, 1385, 1280, 1240, 1180, 915 cm$^{-1}$;

NMR (CDCl$_3$ solution):δ; 4.04 (1H, t), 3.30–2.50 (4H, m), 0.90 (3H, t),

REFERENCE EXAMPLE 18

Methyl 9α-acetoxy-11α-(2-tetrahydropyranyloxy)-15(ξ)-hydroxy-16,16-(1,5-dithiapentano)-prosta-cis-5,trans-13-dienoate 6.9 ml. of a 1.6M solution of n-butyllithium in n-hexane were added dropwise to a solution of 1.76 g. of 2-n-butyl-1,3-dithiane (prepared as described in Reference Example 17) in 30 ml. of tetrahydrofuran under an atmosphere of nitrogen at −20° to −25° C. and the reaction mixture was stirred at the same temperature for 2 hours. The reaction mixture thus obtained was added dropwise at −78° C. to a solution of 3.1 g. of 1α-acetoxy-2α-(6-methoxycarbonylhex-cis-2-enyl)-3β-(2-formyl-trans-vinyl)-4α-(2-tetrahydropyranyloxy)-cyclopentane (prepared as described in Reference Example 8) in 50 ml. of tetrahydrofuran and the reaction mixture was stirred at the same temperture for 1 hour. Then 2 ml. of acetic acid were added to the reaction mixture, which was concentrated under reduced pressure. The residue was diluted with ethyl acetate, washed with water, an aqueous solution of sodium chloride and an aqueous solution of sodium bicarbonate, dried over sodium sulphate and concentrated under reduced pessure. The residue was purified by column chromatography on silica gel using a mixture of benzene and ethyl acetate (4:1) as eluent to give 2.01 g. of the title compound having the following physical characteristics:

IR (liquid film):ν; 3450, 2940, 2860, 1740, 1440, 1380, 1325, 1250, 1135, 1080, 1030, 975, 920 cm$^{-1}$;

NMR (CDCl$_3$ solution):δ; 6.00–5.65 (2H, m), 5.65–5.21 (2H, m), 5.21–4.90 (1H, m), 4.90–4.41 (2H, m), 3,68 (3H, s), 3.20–2.60 (4H, m.), 2.05 (3H, s), 0.90 (3H, t);

TLC (developing solvent, benzene - ethyl acetate = 2:1);

Rf = 0.58.

REFERENCE EXAMPLE 19

Methyl 9α-acetoxy-11α,15(ξ)-bis-(2-tetrahydropyranyloxy)-16,16-(1,5-dithiapentano)-prosta-cis-5,trans-13dienoate 19 mg. of p-toluenesulphonic acid and 4 ml. of 2,3-dihydropyran were added to a solution of 4.97 g. of methyl 9α-acetoxy-11α-(2-tetrahydropyranyloxy)-15(ξ)-hydroxy-16,16-(1,5-dithiapentano)-prosta-cis-5,trans-13-dienoate (prepared as described in Reference Example 18) in 200 ml. of methylene chloride and the reaction mixture was stirred at room temperaure for 20 minutes, diluted with ethyl acetate, washed with an aqueous solution of sodium bicarbonate and an aqueous solution of sodium chloride, dried over sodium sulphate and concentrated under reduced pressure. The residue was purified by column chromotography on silica gel using a mixture of benzene and ethyl acetate (5:1) as eluent to give 4.2 g. of the title compound having the following physical characteristics:

IR (liquid film):$\nu$; 2940, 2860, 1740, 1660, 1455, 1440, 1380, 1360, 1330, 1250, 1200, 1185, 1160, 1140, 1125, 1080, 1040, 1025, 980, 920, 875, 820, cm$^{-1}$;

NMR (CDCl$_3$ solution):$\delta$; 6.10–5.49 (2H, m), 5.49–5.19 (2H, m), 5.19–4.25 (4H, m), 4.25–3.18 (8H, m), 2.04 (3H, s).

EXAMPLE 15

Methyl 9$\alpha$-hydroxy-11$\alpha$,15($\xi$)-bis-(2-tetrahydropyranyloxy)-16,16-(1,5-dithiapentano)-prosta-cis-5,trans-13-dienoate A solution of 4.2 g. of methyl 9$\alpha$-acetoxy-11$\alpha$,15($\xi$)-bis-(2-tetrahydropyranyloxy)-16,16-(1,5-dithiapentano)-prosta-cis-5,trans-13-dienoate (prepared as described in Reference Example 19) in 40 ml. of methanol was stirred with 1.0 g. of potassium carbonate at 40° to 45° C. for 1 hour. The reaction mixture was poured into a chilled mixture of dilute aqueous hydrochloric acid and diethyl ether and extracted with ethyl acetate. The extracts were washed with an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (5:1) as eluent to give 3.11 g. of the title compound having the following physical characteristics:

IR (liquid film)-$\nu$; 3460, 2950, 2870, 1745, 1665, 1460, 1440, 1360, 1330, 1285, 1270, 1250, 1200, 1190, 1160, 1140, 1120, 1080, 1030, 980, 920, 880, 820 cm$^{-1}$;

NMR (CDCl$_3$ solution):$\delta$; 6.00–5.20 (4H, m) 5.10–4.33 (3H, m), 4.33–3.22 (9H, m);

TLC (developing solvent, benzene - ethyl acetate = 2:1).

Rf = 0.52.

EXAMPLE 16

Methyl 9$\alpha$,11$\alpha$,15$\alpha$-Trihydroxy-16,16-(1,5-dithiapentano)-prosta-cis-5,trans-13-dienoate
[16,16-(1,5-Dithiapentano)-PGF$_{2\alpha}$ methyl ester]

1.0 g. of methyl 9$\alpha$-hydroxy-11$\alpha$,15($\xi$)-bis-(2-tetrahydropyranyloxy)-16,16-(1,5-dithiapentano)-prosta-cis-5,trans-13-dienoate (prepared as described in Example 15) were dissolved in a mixture of 2 ml. of tetrahydrofuran and 20 ml. of a 65% aqueous solution of acetic acid and the reaction mixture was stirred at 40° to 45° C. for 2 hours and then extracted with ethyl acetate. The extracts were washed with water, an aqueous solution of sodium bicarbonate and an aqueous solution of sodium chloride, dired over sodium sulphate and concentrated under reduced pressure. The residue was purified by column chromatography on silica gel using a mixture of cyclohexane and ethyl acetate (2:1) as eluent to give 382 mg. of the title compound, having the following physical characteristics, and 190 mg. of the 15$\beta$-hydroxy isomer:

IR (liquid film):$\nu$; 3400, 3000, 2950, 2930, 2860, 1740, 1660, 1435, 1370, 1320, 1280, 1250, 1175, 1100, 1060, 1030, 975 cm$^{-1}$;

NMR (CDCl$_3$ solution):$\nu$; 5.90–5.60 (2H, m), 5.60–5.25 (2H, m), 4.60–4.40 (1H, m) 4.30–3.80 (2H, m), 3.16 (3H, s), 2.70–2.11 (7H, m);

TLC (developing solvent, ethyl acetate);

Rf = 0.44; (Rf of the 15$\beta$-hydroxy isomer = 0.53),

Optical Rotation: $[\alpha]_D^{23}$ = +44.8° (c=1, CHCl$_3$).

EXAMPLE 17

Methyl 9-oxo-11$\alpha$,15($\xi$)-bis-(2-tetrahydropyranyloxy)-16,16-(1,5-dithiapentano)-prosta-cis-5,trans-13-dienoate 2.0 ml. of dimethylsulphide were added to a solution of 1.6 g of N-chlorosuccinimide in 50 ml. of toluene at −25° C. After stirring for 1 hour, a solution of 1.7 g. of methyl 9$\alpha$-hydroxy-11$\alpha$,15($\xi$)-(2-tetrahydropyranyloxy)-16,16-(1,5-dithiapentano)-prosta-cis-5,trans-13-dienoate (prepared as described in Example 15) in 30 ml. of toluene was added and the reaction mixture was stirred at −25° C. for 2 hours. Then a solution of 3.0 ml. of triethylamine in 5 ml. of n-pentane was added to the reaction mixture, which was stirred at the same temperature for 5 minutes and at room temperature for a further 30 minutes, diluted with 20 ml. of diethyl ether and extracted with ethyl acetate. The extracts were washed with chilled aqueous hydrochloric acid, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (7:1) as eluent to give 1.4 g. of the title compound having the following physical characteristics:

IR (liquid film):$\nu$; 2940, f2860, 1745, 1715, 1455, 1440, 1415, 1380, 1360, 1330, 1250, 1200, 1160, 1130, 1080, 1040, 1025, 980, 915, 875, 820 cm$^{-1}$;

TLC (developing solvent, benzene - ethyl acetate = 2:1);

Rf = 0.66.

EXAMPLE 18

Methyl 9-oxo-11$\alpha$,15$\alpha$,-dihydroxy-16,16-(1,5-dithiapentano)-prosta-cis-5,trans-13-dienoate
[16,16-(1,5-Dithiapentano)-PGE$_2$ methyl ester]

1.4 g. of methyl 9-oxo-11$\alpha$,15($\xi$)-bis-(2-tetrahydropyranyloxy)-16,16-(1,5-dithiapentano-prosta-cis-5,-trans-13-dienoate (prepared as described in Example 17) were dissolved in a mixture of 3 ml. of tetrahydrofuran and 30 ml. of a 65% aqueous solution of acetic acid and the reaction mixture was stirred at 40° to 45° C. for 2 hours, diluted with ethyl acetate, washed with water, an aqueous solution of sodium bicarbonate and an aqueous solution of sodium chloride, dried over sodium sulphate and concentrated under reduced pressure. The residue was purified by column chromatography on silica gel using a mixture of cyclohexane and ethyl acetate (5:2) as eluent to give 6.3 mg. of the title compound, having the following physical characteristics, and 275 mg. of the 15$\beta$-hydroxy isomer:

IR (liquid film):$\nu$; 3400, 3000, 2950, 2930, 2860, 1740, 1440, 1380, 1320, 1285, 1250, 1160, 1080, 1050, 980 cm$^{-1}$;

NMR (CDCl$_3$ solution):$\delta$; 6.00–5.75 (2H, m), 5.52–5.28 (2H, m), 4.68–4.48 (1H, m), 4.28–3.92 (1H, m), 3.67 (3H, s), 3.30–2.54 (7H, m);

TLC (developing solvent, benzene - ethyl acetate = 2:3); p0 Rf = 0.36; (Rf of the 15$\beta$-hydroxy isomer = 0.44), Optical Rotation: $[\alpha]_D^{23}$ = −47.0° (c=1, CHCl$_3$).

REFERENCE EXAMPLE 20

1α-Acetoxy-2α-(6-methoxycarbonylhexyl)-3β-(2-formylethyl)-4α-(2-tetrahydropyranyloxy)-cyclopentane 1.0 g. of 5% palladium of carbon was suspended in 50 ml. of methanol and after the air in the apparatus was replaced by hydrogen, a solution of 1.95 g. of 1α-acetoxy-2α-(6-methoxycarbonylhex-cis-2-enyl)-3β-(2-formyl-trans-vinyl)-4α-(2-tetrahydropyranyloxy)-cyclopentane (prepared as described in Reference Example 8) in 10 ml. of methanol was added thereto. Catalytic reduction of the compound was carried out at room temperature under ambient pressure for 1 hour. After completion of the reaction, the catalyst was filtered off and the filtrate was concentrated under reduced pressure to give 1.925 g. of the title compound having the following physical characteristics:

IR (liquid film):$\nu$; 2940, 2855, 2730, 1740, 1440, 1380, 1330, 1255, 1200, 1180, 1140, 1085, 1040, 980, 925, 910, 880, 820 cm$^{-1}$;

NMR (CDCl$_3$ solution):$\delta$; 5.35–4.95 (1H, m), 4.78 –4.35 (1H, m), 4.25–3.20 (6H, m), 10.0–9.80 (1H, broad s);

TLC (developing solvent, benzene - ethyl acetate = 2:1);

Rf = 0.62.

REFERENCE EXAMPLE 21

Methyl 9α-acetoxy-11α-(2-tetrahydropyranyloxy)-15($\xi$)-hydroxy-16,16-(1,5-dithiapentano)-prostanoate 4.3 ml. of a 1.5M solution of n-butyllithium in n-hexane were added dropwise to a solution of 1.05 g. of 2-n-butyl-1,3-dithiane (prepared as described in Reference Example 17) in 14 ml. of tetrahydrofuran under an atmosphere of nitrogen at $-°$ C. to $-25°$ C. and the reaction mixture was stirred at the same temperature for 2 hours. The reaction mixture thus obtained was added dropwise at $-78°$ C. to a solution of 1.925 g. of 1α-acetoxy-2α-(6-methoxycarbonylhexyl-3β-(2-fornyl-ethyl)-4α-(2-tetrahydropyranyloxy)-cyclopentane (prepared as described in Reference Example 20) in 20 ml. of tetrahydrofuran and the reaction mixture was stirred at the same temperature for 1 hour. Then 1 ml. of acetic acid was added to the reaction mixture, which was concentrated under reduced pressure. The residue was dissolved in ethyl acetate, washed with water, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (8:1) as eluent to give 1.5 g. of the title compound having the following physical characteristics:

IR (liquid film):$\nu$; 3450, 2930, 2850, 1740, 1440, 1380, 1250, 1200, 1175, 1135, 1080, 1030, 980, 920, 875, 815 cm$^{-1}$;

NMR (CDCl$_3$ solution):$\delta$; 5.30–4.93 (1H, m), 4.80–4.40 (1H, m), 4.35–3.25 (7H, m), 3.25–2.53 (4H, m), 2.05 (3H, s), 0.90 (3H, t);

TLC (developing solvent, benzene - ethyl acetate = 3:1); Rf = 0.57.

REFERENCE EXAMPLE 22

Methyl 9α-acetoxy-11α,15($\xi$)-bis-(2-tetrahydropyranyloxy)-16,16-(1,5-dithiapentano)-prostanoate By proceeding as described in Reference Example 19 but replacing the methyl 9α-acetoxy-11α-(2-tetrahydropyranyloxy)-15($\xi$)-hydroxy-16,16-(1,5-dithiapentano)-prosta-cis-5,trans-13-dienoate by 2.2 g. of methyl 9α-acetoxy-11α-(2-tetrahydropyranyloxy)-15($\xi$)-hydroxy-16,16-(1,5-dithiapentano)-prostanoate (prepared as described in Reference Example 21) dissolved in 20 ml. of methylene chloride and utilising 8 mg. of p-toluenesulphonic acid and 0.7 ml. of 2,3-dihydropyran there were obtained, without purification by column chromatography, 2.5 g. of the title compound, having the following physical characteristics:

IR (liquid film):$\nu$; 2940, 2850, 1740, 1450, 1440, 1380, 1360, 1325, 1250, 1200, 1160, 1135, 1080, 1040, 975, 910, 875 cm$^{-1}$;

NMR (CDCl$_3$ solution):$\delta$; 5.36–4.40 (3H, m), 4.40 –3.20 (9H, m);

TLC (developing solvent, benzene - ethyl acetate = 4:1); Rf = 0.60.

EXAMPLE 19

Methyl 9α-hydroxy-11α,15($\xi$)-bis-(2-tetrahydropyranyloxy)-16,16-(1,5-dithiapentano)-prostanoate By proceeding as described in Example 15 but replacing the methyl 9α-acetoxy-11α,15($\xi$)-bis-(2-tetrahydropyranyloxy)-16,16-(1,5-dithiapentano)-prosta-cis-5,trans-13-dienoate by 2.5 g. of methyl 9α-acetoxy-11α,15($\xi$)-bis-(2-tetrahydropyranyloxy)-16,16-(1,5-dithiapentano)-prostanoate (prepared as described in Reference Example 22) dissolved in 30 ml. of methanol and stirred with 200 mg. of potassium carbonate at 45° to 50° C. for 1.5 hours, and using a mixture of benzene and ethyl acetate (7:1) as eluent there were obtained 889 mg. of the title compound having the following physical characteristics:

IR (liquid film):$\nu$; 3530, 2940, 2850, 1740, 1650, 1625, 1480, 1455, 1440, 1380, 1360, 1330, 1280, 1250, 1200, 1180, 1160, 1135, 1080, 1035, 990, 915, 875, 820 cm$^{-1}$;

NMR (CDCl$_3$ solution):$\delta$; 5.10–4.50 (2H, m), 4.40–3.23 (10H, m);

TLC (developing solvent, benzene - ethyl acetate = 4:1); Rf = 0.40.

EXAMPLE 20

Methyl 9α,11α,15($\xi$)-trihydroxy-16,16-(1,5-dithiapentano)prostanoate

[16,16-(1,5-Dithiapentano)-13,14-dihydro-15($\xi$)-PGF$_{1\alpha}$methyl ester]

By proceeding as described in Example 18, but replacing the methyl 9-oxo-11α,15($\xi$)-bis-(2-tetrahydropyranyloxy)-16,16-(1,5-dithiapentano)-prosta-cis-5,trans-13-dienoate by 423 mg. of methyl 9α-hydroxy-11α,15($\xi$)-bis-(2-tetrahydropyranyloxy)-16,16-(1,5-dithiapentano)-prostanoate (prepared as described in Example 19) and utilising a mixture of 1 ml of tetrahydrofuran and 10 ml. of a 65% aqueous solution of acetic acid, and using a mixture of cyclohexane and ethyl acetate (2:1) as eluent there were obtained 280 mg. of the title compound having the following physical characteristics:

IR (liquid film):ν; 3430, 2940, 2850, 1740, 1440, 1285, 1260, 1200, 1180, 1120, 1080 cm$^{-1}$;

NMR (CDCl$_3$ solution):δ; 4.45–3.80 (3H, m), 3.65 (3H, s), 3.30–2.60 (7H, m);

TLC (developing solvent, benzene - ethyl acetate = 2:3); Rf = 0.41.

EXAMPLE 21

Methyl 9α-oxo-11α,15(ξ)-bis-(2-tetrahydropyranyloxy)-16,16-(1,5-dithiapentano)-prostanoate 0.5 ml. of dimethylsulphide was added to a solution of 400 mg. of N-chlorosuccinimide in 15 ml. of toluene at −25° C. and the solution was stirred at −20° to −25° C. for 1 hours. To the solution thus obtained, a solution of 465 mg. of methyl 9α-hydroxy-11α,15(ξ)-bis-(2-tetrahydropranyloxy)-16,16-(1,5-dithiapentano)-prostanoate (prepared as described in Example 19) in 10 ml. of toluene was added and the reaction mixture was stirred at −25° C. for 2 hours. Then a solution of 1 ml. of triethylamine in 1.5 ml. of n-pentane was added to the reaction mixture, which was stirred at room temperature for 10 minutes, diluted with 10 ml. of diethyl ether, stirred for a further 10 minutes, and then diluted with ethyl acetate. The mixture was then washed successively with chilled dilute aqueous hydrochloric acid, chilled water, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (8:1) as eluent to give 346 mg. of the title compound having the following physical characteristics.

IR (liquid film): ν; 2930, 2850, 1740, 1710, 1450, 1435, 1375, 1355, 1325, 1280, 1245, 1200, 1160, 1135, 1080, 1035, 980, 915, 870, 815 cm$^{-1}$;

NMR (CDCl$_3$ solution): δ; 5.00–4.42 (2H, m), 4.42–3.20 (9H, m);

TLC (developing solvent, benzene - ethyl acetate = 4:1); Rf = 0.49.

EXAMPLE 22

Methyl 9-oxo-11α,15(86)-dihydroxy-16,16-(1,5-dithiapenanto)prostanoate [16,16-(1,5-Dithiapentano)-13,14-dihydro-15(ξ)-PGE$_1$ methyl ester]

By proceeding as described in Example 18 but replacing the methyl 9-oxo-11α,15(ξ)-bis-(2-tetrahydropyranyloxy)-16,16-(1,5-dithiapentano)-prosta-cis-5,trans-13-dienoate by 346 mg. of methyl 9-oxo-11α,15(ξ)-bis-(2-tetrahydropyranyloxy)-16,16-(1,5-dithiapentano)prostanoate (prepared as described in Example 21) dissolved in a mixture of 1 ml. of tetrahydrofuran and 10 ml. of a 65% aqueous solution of acetic acid, stirring the reaction mixture at 40° to 45° C. for 1.5 hours, and using a mixture of cyclohexane and ethyl acetate (2:1) as eluent there were obtained 240 mg. of the title compound having the following physical characteristics:

IR (liquid film): ν; 3430, 2940, 2850, 1740, 1455, 1440, 1420, 1380, 1330, 1285, 1245, 1200, 1175, 1120, 1080, 1050, 1020 cm$^{-1}$;

NMR (CDCl$_3$ solution): δ; 4.40–3.80 (2H, m), 3.65 (3H, s), 3.20–2.58 (7H, m);

TLC (developing solvent, benzene - ethyl acetate = 2:3); Rf = 0.49.

REFERENCE EXAMPLE 23

Methyl 9α,11α,15(ξ)-trihydroxy-16-oxo-prostanoate [16-Oxo-13,14-dihydro-15(ξ)-PGF$_{1α}$ methyl ester]

Under an atmosphere of nitrogen, a solution of 280 mg. of 16,16-(1,5-dithiapentano)-13,14-dihydro-15(ξ)-PGF$_{1=}$ methyl ester (prepared as described in Example 20) in 5 ml. of acetonitrile was added dropwise at 0° C. to a solution of 243 mg. of N-chlorosuccinimide and 348 mg. of silver nitrate in a mixture of 10 ml. of acetonitrile and 4 ml. of water. After stirring for 25 minutes, 1 ml. of dimethyl sulphoxide was added to the reaction mixture, which was then stirred for 30 minutes at room temperature. The reaction mixture was extracted with a mixture of ethyl acetate and diethyl ether (1:2). The extracts were washed with a saturated aqueous solution of ammonium chloride, water and an aqueous solution of sodium chloride, dried over sodium sulphate and concentrated under reduced pressure. The residue was purified by column chromatography on silica gel using a mixture of cyclohexane and ethyl acetate (1:1) as eluent to give 74 mg. of the title compound having the following physical characteristics:

IR (liquid film): ν; 3400, 2920, 2840, 1735, 1710, 1640, 1460, 1450, 1435, 1360, 1260, 1200, 1170, 1115, 1070, 1040 cm$^{-1}$;

NMR (CDCl$_3$ solution): δ; 4.28–3.75 (3H, m), 3.64 (3H, s), 2.78 (3H, broad s), 2.47 (2H, t), 2.29 (2H, t);

TLC (developing solvent, benzene - ethyl acetate = 2:3); Rf = 0.21.

REFERENCE EXAMPLE 24

Methyl 9,16-dioxo-11α,15(ξ)-dihydroxy-prostanoate [16-oxo-13,14-dihydro-15(ξ)-PGE$_1$ methyl ester]

Proceeding as described in Reference Example 23, but replacing the 16,16(1,5-dithiapentano)13,14-dihydro-15(ξ)-PGF$_{1α}$ methyl ester by 240 mg. of 16,16-(1,5-dithiapentano)-13,14-dihydro-15(ξ)-PGE$_1$ methyl ester (prepared as described in Example 22) dissolved in 5 ml. of acetonitrile, utilising a solution of 243 mg. of N-chlorosuccinimde and 348 mg. of silver nitrate in a mixture of 10 ml. of acetonitrile and 4 ml. of water and using a mixture of cyclohexane and ethyl acetate (5:2) as eluent there were obtained 63 mg. of the title compound having the following physical characteristics:

IR (liquid film): ν; 3430, 2930, 2850, 1740, 1640, 1435, 1400, 1360, 1245, 1200, 1170, 1120, 1075 cm$^{-1}$;

NMR (CDCl$_3$ solution): δ; 4.35–3.95 (2H, m), 3.63 (3H, s), 3.03–2.58 (3H, m), 2.48 (2H, t), 2.28 (2H, t);

TLC (developing solvent, benzene - ethyl acetate = 2:3); Rf = 0.44.

REFERENCE EXAMPLE 25

Methyl 9α-acetoxy-11α-(2-tetrahydropyranyloxy)-15(ξ)-hydroxy-16(ξ)-phenylthio-16-methylthio-17,18,19,20-tetranorprostanoate By proceeding as described in Reference Example 9 but utilising the reaction mixture obtained from 2.35 ml. of a 1.4M solution of n-butyllithium in n-hexane and a solution of 0.491 ml. of phenylthiomethylthio-methane (prepared as described in Reference Example 1) in 6 ml. of tetrahydrofuran and replacing the 1α-acetoxy-2α-(6-methoxycarbonylhex-cis-2-enyl)-3β-(2-formyl-transvinyl)-4α-(2-tetrahydropyranyloxy)cyclopentane by 700 mg. of 1α-acetoxy-2α-(6-methoxycarbonylhexyl)-3β-(2-formyl-ethyl)-4α-(2-tetrahydropyranyloxy)-cyclopentane (prepared as described in Reference Example 20) dissolved in 12 ml. of tetrahydrofuran and stirring the reaction mixture at −70° C. for 1.5 hours and at room temperature for 20 minutes, and using a mixture of benzene and ethyl acetate (6:1) as eluent there were obtained 400 mg. of the title compound having the following physical characteristics:

IR (liquid film): ν; 3450, 1740, 1590, 1440, 1260, 1030 760 cm$^{-1}$;

NMR (CDCl$_3$ solution): δ; 60–7.00 (5H, m) 5.20–4.85 (1H, m), 4.70–4.35 (1H, m), 3.63 (3H, s), 2.22 (1.5H, s), 2.12 (1.5H, s), 2.02 (3H, s).

REFERENCE EXAMPLE 26

Methyl 9α-acetoxy-11α,15(ξ)-bis-(2-tetrahydropyranyloxy)-16(ξ)-phenylthio-16-methylthio-17,18,19,20-tetranorprostanoate By proceeding as described in Reference Example 10 but utilising 0.1 ml. of 2,3-dihydropyran and a small amount of p-toluenesulphonic acid, replacing the methyl 9α-acetoxy-11α,15α-dihydroxy-16(ξ)-phenylthio-16-methylthio-17,18,19,20-tetranorprosta-cis-5,trans-13-dienoate by 255 mg. of methyl 9α-acetoxy-11α-(2-tetrahydropyranyloxy)-16(ξ)-hydroxy-16(ξ)-phenylthio-16-methylthio-17,18,19,20-tetranorprostanoate (prepared as described in Reference Example 25) dissolved in 3 ml. of methylene chloride and using a mixture of benzene and ethyl acetate (15:1) as eluent there were obtained 200 mg. of the title compound having the following physical characteristics:

IR (liquid film): ν; 1740, 1590, 1440, 1250, 1030, 760 cm$^{-1}$;

NMR (CDCl$_3$ solution: δ; 7.60–7.00 (5H, m), 5.15–4.80 (1H, m) 4.80–4.40 (2H, m), 3.62 (3H, s), 2.25 (1.5H, s), 2.20 (1.5H, s), 2.02 (3H, s).

EXAMPLE 23

Methyl 9α-hydroxy-11α,15(ξ)-bis-(2-tetrahydropyranyloxy)-16(ξ)-phenylthio-16-methylthio-17,18,19,20-tetranorprostanoate By proceeding as described in Example 3 but replacing the methyl 9α-acetoxy-11α,15α-bis-(2-tetrahydropyranyloxy)-16(ξ)-phenylthio-16-methylthio-17,18,19,20-tetranorprosta-cis-5, trans-13-dienoate by 200 mg. of methyl 9α-acetoxy-11α,15(ξ)-bis-(2-tetrahydropyranyloxy)-16(ξ)-phenylthio-16-methylthio-17,18,19,20-tetranorprostanoate (prepared as described in Reference Example 26) dissolved in 3 ml. of methanol, utilising 50 mg. of anhydrous potassium carbonate and purifying the product by column chromatography on silica gel using a mixture of benzene and ethyl acetate (5:1) as eluent there were obtained 147 mg. of the title compound having the following physical characteristics:

IR (liquid film): ν; 3450, 1740, 1590, 1440, 1030, 760 cm$^{-1}$;

NMR (CDCl$_3$ solution): δ; 7.60–7.00 (5H, m), 4.80–4.40 (2H, m) 3.62 (3H, s), 2.24 (1.5H s), 2.20 (1.5H, s).

EXAMPLE 24

Methyl 9-oxo-11α,15(ξ)-bis-(2-tetrahydropyranyloxy)-16(ξ)-phenylthio-16-methylthio-17,18,19,20-tetranorprostanoate By proceeding as described in Example 4 but utilising 0.152 ml. of dimethylsulphide and 117 mg. of N-chlorosuccinimide in 3.7 ml. of toluene, replacing the methyl 9α-hydroxy-11α,15α-bis-(2-tetrahydropyranyloxy)-16(ξ)-phenylthio-16-methylthio-17,18,19,20-tetranorprosta-cis-5,trans-13-dienoate by 110 mg. of methyl 9α-hydroxy-11α,15(ξ)-bis-(2-tetrahydropyranyloxy)-16(ξ)-phenylthio-16-methylthio-17,18,19,20-tetranorprostanoate (prepared as described in Example 23) dissolved in 1.5 ml. of toluene and utilising a solution of 0.217 ml. of triethylamine in 0.31 ml. of n-pentane there were obtained, without purification by column chromatography, 90 mg. of the title compound having the following physical characteristics:

IR (liquid film): ν; 1740, 1710, 1590, 1440, 1030, 760 cm$^{-1}$;

NMR (CDCl$_3$ solution): δ; 7.60–7.00 (5H, m), 4.80–4.40 (2H, m), 3.62 (3H, s), 2.24 (1.5H, s), 2.20 (1.5H, s).

EXAMPLE 25

Methyl 9-oxo-11α,15(ξ)-dihydroxy-16(ξ)-phenylthio-16-methylthio-17,18,19,20-tetranorprostanoate

[16(ξ)-Phenylthio-16-methylthio-17,18,19,20-tetranor-13,14-dihydro-15(ξ)-PGE$_1$ methyl ester ]

90 mg. of methyl 9-oxo-11α,15(ξ)-bis-(2-tetrahydropyranyloxy)-16(ξ)-phenylthio-16-methylthio-17,18,19,20-tetranorprostanoate (prepared as described in Example 24) were dissolved in a mixture of 0.35 ml. of tetrahydrofuran and 2.25 ml. of a 65% aqueous solution of acetic acid and the reaction mixture was stirred at 40° C. for 1.5 hours, poured into water and extracted with ethyl acetate. The extracts were washed with an aqueous solution of sodium bicarbonate, water and an aqueous solution of sodium chloride, dried over magnesium sulphate and concentrated under reduced pressure. The residue was purified by column chromatography on silica gel using a mixture of ethyl acetate and cyclohexane (1:3) as eluent to give 42 mg. of the title compound having the following physical characteristics:

TLC (developing solvent, ethyl acetate - cyclohexane = 5:1); Rf = 0.50;

IR (liquid film): ν; 3400, 1740, 1590, 1440, 760 cm$^{-1}$;
NMR (CDCl$_3$ solution): δ; 7.59–7.25 (5H, m), 4.25–3.95 (2H, m), 3.90–3.70 (1H, m), 3.67 (3H, s), 3.20–2.50 (3H, m), 2.27 (1.5H, s), 2.26 (1.5H, s).

The present invention includes within its scope pharmaceutical compositions which comprise at least one new thereapeutically useful compound of general formula VI, or cyclodextrin clathrate or non-toxic salt thereof, together with a pharmaceutical carrier or coating. In clinical practice the new compounds of the present invention will normally be administered orally, vaginally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration inlcude pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorportion of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the doses per person are generally between 0.01 and 5 mg. by oral administration in the treatment of hypertension, between 0.5 and 100 μg. by oral administration in the treatment of gastric ulceration, and between 0.001 and 50 mg. by oral, intravaginal, intravenous and extra-amniotic administration for contraception and menstrual regulation in female mammals and in the termination of pregnancy and the induction of labour in pregnant female mammals.

Prostaglandin compounds according to the present invention may be administered orally by any method known per se for administration by inhalation of drugs which are not themselves gaseous under normal conditions of administrtion. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 1 to 100 μg., and more particularly 10 to 50 μg., of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Means for producing self-propelling compositions for generating aerosols for administration as medicaments are, for example, described in detail in U.S. Pat. Nos. 2,868,691 and 3,095,355.

The following Example illustrates pharmaceutical compositions according to the invention.

EXAMPLE 26

16(ξ)-Phenylthio-16-methylthio-17,18,19,20-tetranor-PGE$_2$ methyl ester (2 mg.) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica; 200 mg.) was added and the powder obtained was machine-filled into forty No. 2 hard gelatin capsules to give capsules each containing 50 μg. of 16(ξ)-phenylthio-16-methylthio-17,18,19,20-tetranor-PGE$_2$ methyl ester which after swallowing of the capsules is released into the stomach.

We claim:

1. A compound of the formula:

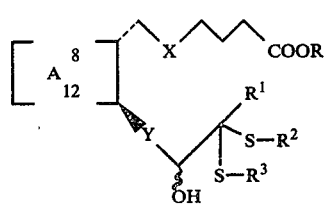

wherein A represents a grouping of the formula:

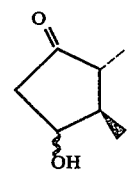

x represents ethylene, Y represents trans-vinylene, R represents a hydrogen atom or a straight- or branched-chain alkyl group containing from 1 to 12 carbon atoms, $R^1$ represents a hydrogen atom or a straight- or branched-chain alkyl groups containing from 1 to 10 carbon atoms, $R^2$ represents a straight- or branched-chain alkyl group containing from 1 to 4 carbon atoms, $R^3$ represents a grouping of the formula:

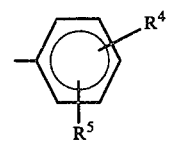

wherein $R^4$ and $R_5$ each represents a hydrogen or halogen atom, a trifluoromethyl group or an alkyl group containing from 1 to 3 carbon atoms and cyclodextrin clathrates of such acids and esters and, when R represents a hydrogen atom, non-toxic salts of such acids.

2. A compound according to claim 1 wherein R represents a hydrogen atom or a methyl group.

3. A compound according to claim 1 wherein $R_1$ represents a hydrogen atom or a straight- or branched-chain alkyl group of 1 to 4 carbon atoms.

4. A compound according to claim 1 wherein $R^2$ represents a straight- or branched-chain alkyl group of from 1 to 4 carbon atoms and $R^3$ represents a phenyl group.

5. A compound according to claim 1 which is 16(ξ)-phenylthio-16-methylthio-17,18,19,20-tetranor-PGE$_1$ methyl ester.

* * * * *